United States Patent [19]

Kistner et al.

[11] Patent Number: 5,658,491

[45] Date of Patent: Aug. 19, 1997

[54] PROCESS FOR CONTROLLING CONE TILT ANGLE IN MIXTURES OF SMECTIC LIQUID CRYSTAL COMPOUNDS

[75] Inventors: John F. Kistner; Marc D. Radcliffe, both of Woodbury; Patricia M. Savu, Maplewood; Daniel C. Snustad, Woodbury, all of Minn.

[73] Assignee: Minnesota Mining and Manufacturing Company, St. Paul, Minn.

[21] Appl. No.: 542,179

[22] Filed: Oct. 12, 1995

[51] Int. Cl.[6] .......................... C09K 19/06; C09K 19/34; C09K 19/12; C09K 19/32

[52] U.S. Cl. .................. 252/299.01; 252/299.6; 252/299.61; 252/299.66; 252/299.62; 252/29.63; 252/299.65; 252/299.67

[58] Field of Search .............. 252/299.01, 299.6, 252/299.61, 299.66, 299.62, 299.63, 299.65, 299.67

[56] References Cited

U.S. PATENT DOCUMENTS

| | | | |
|---|---|---|---|
| 2,519,983 | 8/1950 | Simons | 204/62 |
| 3,470,258 | 9/1969 | Tesoro | 260/615 |
| 4,001,137 | 1/1977 | Steinstrasser | 252/299.64 |
| 4,011,173 | 3/1977 | Steinstrasser | 252/299.64 |
| 4,113,647 | 9/1978 | Coates et al. | 252/299.5 |
| 4,202,791 | 5/1980 | Sato et al. | 252/299.5 |
| 4,256,656 | 3/1981 | Beguim et al. | 558/416 |
| 4,330,426 | 5/1982 | Eidenschink et al. | 252/299.63 |
| 4,367,924 | 1/1983 | Clark et al. | 359/564 |
| 4,393,231 | 7/1983 | Misaki et al. | 560/73 |
| 4,400,293 | 8/1983 | Romer et al. | 252/299.63 |
| 4,411,494 | 10/1983 | Crossland et al. | 359/74 X |
| 4,419,664 | 12/1983 | Crossland et al. | 345/94 X |
| 4,439,015 | 3/1984 | Rich et al. | 359/103 |
| 4,481,149 | 11/1984 | Misaki et al. | 558/416 |
| 4,528,562 | 7/1985 | Crossland et al. | 345/209 |
| 4,564,694 | 1/1986 | Hirai et al. | 560/1 |
| 4,572,794 | 2/1986 | Eidenschink et al. | 252/299.2 |
| 4,576,732 | 3/1986 | Isogai et al. | 252/299.65 |
| 4,592,858 | 6/1986 | Higuchi et al. | 252/299.66 |
| 4,613,209 | 9/1986 | Goodby et al. | 359/104 |
| 4,614,608 | 9/1986 | Le Barny et al. | 252/299.64 |
| 4,617,140 | 10/1986 | Eidenschink et al. | 252/299.61 |
| 4,668,427 | 5/1987 | Saito et al. | 252/299.66 |
| 4,780,242 | 10/1988 | Miyazawa et al. | 252/299.65 |
| 4,816,178 | 3/1989 | Katagiri et al. | 252/299.6 |
| 4,816,596 | 3/1989 | Langlois | 358/423 |
| 4,837,364 | 6/1989 | Desbois et al. | 568/43 |
| 4,876,027 | 10/1989 | Yoshinaga et al. | 252/299.65 |
| 4,879,060 | 11/1989 | Shionozaki et al. | 252/299.61 |
| 4,886,619 | 12/1989 | Janulis | 252/299.1 |
| 4,914,224 | 4/1990 | Shoji et al. | 560/65 |
| 5,051,527 | 9/1991 | Suzuki et al. | 560/51 |
| 5,062,691 | 11/1991 | Tristani-Kendra et al. | 359/56 |
| 5,082,587 | 1/1992 | Janulis | 252/299.01 |
| 5,141,669 | 8/1992 | Bloom et al. | 252/299.65 |
| 5,167,859 | 12/1992 | Wachtler et al. | 252/299.61 |
| 5,194,179 | 3/1993 | Suzuki et al. | 252/299.66 |
| 5,196,140 | 3/1993 | Poetsch et al. | 252/299.6 |
| 5,252,695 | 10/1993 | Niciri et al. | 528/30 |
| 5,262,082 | 11/1993 | Janulis et al. | 252/299.01 |
| 5,348,677 | 9/1994 | Poetsch et al. | 252/299.6 |
| 5,362,919 | 11/1994 | Costello et al. | 568/601 |
| 5,377,033 | 12/1994 | Radcliffe | 359/75 |
| 5,399,291 | 3/1995 | Janulis et al. | 252/299.01 |
| 5,417,883 | 5/1995 | Epstein et al. | 252/299.01 |
| 5,437,812 | 8/1995 | Janulis et al. | 252/299.01 |
| 5,474,705 | 12/1995 | Janulis et al. | 252/299.01 |
| 5,482,650 | 1/1996 | Janulis et al. | 252/299.01 |

FOREIGN PATENT DOCUMENTS

| | | |
|---|---|---|
| 0 047 877 | 3/1982 | European Pat. Off. . |
| 0 163 229 | 12/1985 | European Pat. Off. . |
| 0 181 601 | 5/1986 | European Pat. Off. . |
| 0 220 747 | 5/1987 | European Pat. Off. . |
| 0 332 025 | 9/1989 | European Pat. Off. . |
| 0 548 548 | 6/1993 | European Pat. Off. . |
| 0 641 850 | 8/1995 | European Pat. Off. . |
| 33 32 692 | 3/1985 | Germany . |
| 40 34 123 | 4/1992 | Germany . |
| 57-165334 | 10/1982 | Japan . |
| 1-104031 | 4/1989 | Japan . |
| 2-69443 | 3/1990 | Japan . |
| WO88/03530 | 5/1988 | WIPO . |
| WO88/05803 | 8/1988 | WIPO . |
| WO88/08441 | 11/1988 | WIPO . |
| WO91/00897 | 1/1991 | WIPO . |
| WO91/11418 | 8/1991 | WIPO . |

OTHER PUBLICATIONS

Jajer et al., Synthesis 1990, 556.
Chaudhary et al., Tetrahedron Letters 1979, 95.
Middleton, J. Org. Chem. 40, 574 (1975).
Sakaguchi et al., Ferroelectrics 114, 265 (1991).
Byun et al., Tet. Lett. 30, 2751 (1989).

(List continued on next page.)

*Primary Examiner*—C. H. Kelly
*Attorney, Agent, or Firm*—Gary L. Griswold; Walter N. Kirn; Lucy C. Weiss

[57] ABSTRACT

A process for controlling the cone tilt angle of a tilted smectic liquid crystal composition comprises the step of combining (a) at least one liquid crystal composition comprising at least one smectic or latent smectic liquid crystal compound comprising (i) an aliphatic fluorocarbon terminal portion comprising a terminal fluoroalkyl or fluoroether group and an alkylene group having at least two carbon atoms and containing at least one catenary ether oxygen atom, (ii) an aliphatic hydrocarbon terminal portion, and (iii) a central core connecting the terminal portions; and (b) at least one liquid crystal composition comprising at least one smectic or latent smectic liquid crystal compound; with the provisos that at least one of the compositions (a) and (b) comprises at least one chiral liquid crystal compound and that the combining of compositions (a) and (b) provides an optically active, tilted chiral smectic liquid crystal composition. The process enables control of cone tilt angle and thereby control of the brightness characteristics of liquid crystal display devices.

29 Claims, No Drawings

OTHER PUBLICATIONS

Gray et al., J. Chem. Soc., Perkin Trans. II 1989, 2041.

Iwakura et al., J. Org. Chem. 29, 379 (1964).

Miyasato et al., Jap. J. Appl. Phys. 22, L 661 (1983).

H. Nohira et al., Mol. Cryst. Liq. Cryst. 180B, 379–88 (1990).

"Antiferroelectric Chiral Smectic Liquid Crystals", Fukuda et al., J. Mater. Chem. 4(7), 997 (1994).

"Effect of Chiral End Group Variation on the Properties of Ferroelectric Copolymers", Naciri et al., Ferroelectrics 148, 297 (1993).

Pelzl et al., Kristall Technik. 14, 817(1979).

Pelzl et al., Liquid Crystals 2, 131 (1987).

Sierra et al., J. Am. Chem. Soc. 114, 7645 (1992).

Meyer, R.B. et al., J. Physique 36, L–69 (1975).

Zaschke, H. and Stolle, R., "Synthese niedrigschmelzender Kristallin–Flussiger Hetercyclen; 5–n–Alkyl–2–[4–n–alkanoyloxy–phenyl]pyrimidine", Z. Chem. 15, 441–43 (1975).

Mochizuki, A. et al., SPIE 1665 108–09 (1992).

Pelzl, G. et al., Mol. Cryst. Liq Cryst. 53, 167 (1979).

Clark, N.A. et al, Appl. Phys. Lett. 36, 899 (1980).

Holy, A. and Z. Arnold, Collection Chzechoslov. Chem. Commun. 38, 1371 (1973).

Kahn, F.J., Appl. Phys. Lett. 22, 111 (1973).

Lagerwall et al., 1st International Symposium On Ferroelectric Liquid Crystals, Bordeaux–Arcachon, France, 1987.

Partridge, M.W., and W.F. Short, J. Chem. Soc., 390 (1947).

P.M. Savu, Kirk–Othmer Encyclopedia of Chemical Technology, Fourth Edition, vol. 11, pp. 558–564, John Wiley & Sons, New York (1994).

Knunyants, I.L., L. Chih–yuan and V.V. Shokina, Advances in Chem. (Uspekhi Khimi) 32, original 1502, Eng. Trans, 461–76 (1963) Translation RSIC–165 (Redstone Information Center).

Arnold, Z. and F. Sorm, Coll. Czech. Chem. Commun. 23, 452 (1958).

Abe, T., and S. Nagase, "Electrochemical Fluorination (Simons Process) as a Route to Perfluorinated Organic Compounds of Industrial Interest," Preparation,Properties and Industrial Applications of Organofluorine Compounds, 37–38 (1982).

Patent Abstracts of Japan, vol. 15, No. 271 (C–0848), Jul. 10, 1991.

Molecular Crystals Liquid Crystals 47, 1 (1978).

Molecular Crystals Liquid Crystals 67, 235 (9181).

"The Silicon Liquid–Crystal Light Value", J Appl. Phys. 57(4), 1356 (1985).

"Smectic Liquid Crystal from (Perfluorodecyl)decane", Molecular Crystals Liquid Crystals 2 (3–4), 111 (1985).

Molecular Crystals Liquid Crystals 114, 237 (1984).

J. Am. Chem. Soc. 86, 964 (1964).

Jap. Journal of Applied Physics 24 (11), 1389 (1985).

J.W. Goodby and T.M. Leslie, "Some Novel Ferroelectric Smectic Liquid Crystals", Liquid Crystals & Ordered Fluids, vol. 4, pp. 1–32, Plenum Press, New York.

Gray, G.W., Liquid Crystals & Plastic Crystals, vol. 1, pp. 142–143, Ellis Horwood Limited (1974).

Zverkova, T.I. et al., Advances in Liquid Crystal Research & Applications, Pergamon Press, Oxford, pp. 991–995 (1980).

LeBarny, P. et al., Molecular Crystals and Liquid Crystals 127, 413 (1985).

Streitweiser, A. et al., Introduction to Organic Chemistry, pp.378–380, 480, 837, Macmillan Publishing Co., New York (1976).

Sirutkaitis, R. et al., Advances in Liquid Crystal Research and Applications, Pergamon Press, Oxford, pp. 1023–1028 (1980).

Schiller et al., Liquid Crystals 2,21 (1987).

PROCESS FOR CONTROLLING CONE TILT ANGLE IN MIXTURES OF SMECTIC LIQUID CRYSTAL COMPOUNDS

FIELD OF THE INVENTION

This invention relates to a process for preparing mixtures of smectic or latent smectic liquid crystal compounds having a controlled cone tilt angle. In other aspects, this invention relates to fluorinated, smectic or latent smectic liquid crystal compounds useful in the process; to mixtures prepared by the process; and to electrooptical display devices containing the mixtures.

BACKGROUND OF THE INVENTION

Devices employing liquid crystals have found use in a variety of electrooptical applications, in particular those which require compact, energy-efficient, voltage-controlled light valves, e.g., watch and calculator displays, as well as the flat-panel displays found in portable computers and compact televisions. Liquid crystal displays have a number of unique characteristics, including low voltage and low power of operation, which make them the most promising of the non-emissive electrooptical display candidates currently available.

One of the most important characteristics of a liquid crystal display device is its response time, i.e., the time required for the device to switch from the on (light) state to the off (dark) state. In a ferroelectric or anti-ferroelectric device, response time ($\tau=\eta \sin^2\Theta/P_sE$) is proportional to the rotational viscosity ($\eta$) of the liquid crystal Compound(s) contained within the device, is also proportional to the square of the sine of the cone tilt angle ($\Theta$) of a tilted smectic mesophase of the compounds, and is inversely proportional to the polarization ($P_s$) of the compounds and to the applied electric field (E). Thus, response time can be reduced by using compound(s) having high polarizations and/or low viscosities and/or low cone tilt angles, and such compounds are greatly desired in the art.

Other important characteristics of a liquid crystal display device are its brightness and contrast ratio. High brightness and contrast ratios provide enhanced optical discrimination and viewing ease and are therefore preferred. Brightness is related to the intensity of light transmitted through a device, which for a surface-stabilized ferroelectric device (as described in U.S. Pat. No. 4,367,924, the description of which is incorporated by reference herein) with two polarizers can be represented by the equation $$I = I_o (\sin^2(4\Theta))(\sin^2(\pi\Delta nd/\lambda)),$$

where $I_o$=transmission through parallel polarizers, $\Theta$=liquid crystal cone tilt angle, $\Delta n$=liquid crystal birefringence, $d$=device spacing, and $\lambda$=wavelength of light used. The maximum transmission is obtained when both the terms $\sin^2(4\Theta)$ and $\sin^2(\pi\Delta nd/\lambda)$ are at a maximum (each term equals one). Since the first term is at a maximum when the liquid crystal composition in the device has a cone tilt angle of 22.5 degrees, liquid crystal compounds which have cone tilt angles close to 22.5 degrees (or which can be mixed with other liquid crystal compounds to form compositions having cone tilt angles close to 22.5 degrees) are also highly desired in the art.

In particular, since many fluorine-containing liquid crystal compounds have cone tilt angles which exceed the optimum value of 22.5 degrees, materials and methods for reducing cone tilt angle are needed. Although hydrocarbon liquid crystal compounds have low cone tilt angles (below 22.5 degrees), they generally cannot be used for this purpose due to their incompatibility with fluorine-containing liquid crystal compounds (which generally leads to loss of the active mesophase).

In addition to fast response times and optimized tilt angles, liquid crystal compounds should ideally possess broad smectic temperature ranges (to enable operation of a display device over a broad range of temperatures) or should be capable of combination with other liquid crystal compounds without adversely affecting the smectic phase behavior of the base mixture.

SUMMARY OF THE INVENTION

It has been discovered that the cone tilt angle of certain fluorine-containing liquid crystal compounds can surprisingly be reduced (and the smectic C mesophase often surprisingly broadened) by inserting an extended hydrocarbon ether group adjacent to a terminal fluoroalkyl or fluoroether group. It has also been discovered that such compounds (as well as those which do not exhibit a smectic C mesophase) can be used in admixture with certain other liquid crystal compounds to control or adjust the cone tilt angle of the resultant mixture without significant adverse effect on the smectic C mesophase of the base composition.

Thus, in one aspect, this invention provides a process for controlling the cone tilt angle of a tilted smectic liquid crystal composition while substantially maintaining or even improving the temperature range of the tilted smectic mesophase of the composition. The process comprises the step of combining (a) at least one liquid crystal composition comprising at least one smectic or latent smectic liquid crystal compound comprising (i) an aliphatic fluorocarbon terminal portion comprising a terminal fluoroalkyl or fluoroether group and an alkylene group having at least two carbon atoms and containing at least one catenary (i.e., in-chain and bonded only to carbon atoms) ether oxygen atom, (ii) an aliphatic hydrocarbon terminal portion, and (iii) a central core connecting the terminal portions; and (b) at least one liquid crystal composition comprising at least one smectic or latent smectic liquid crystal compound; with the provisos that at least one of the compositions (a) and (b) comprises at least one chiral liquid crystal compound and that the combining of compositions (a) and (b) provides an optically active, tilted chiral smectic liquid crystal composition. (Latent smectic liquid crystal compounds are those which by themselves may not exhibit certain smectic mesophase(s), e.g., tilted smectic mesophase(s), but which, when in admixture with compounds having smectic mesophases or with other compounds having latent smectic mesophases, develop or exhibit smectic mesophases under appropriate conditions.) Preferably, the former composition (s) (i.e., composition(s) (a)) are utilized in amount(s) such that the resulting combination has a cone tilt angle between about 10 and about 35 degrees. Composition(s) (b) preferably comprise at least one fluorine-containing liquid crystal compound.

The process of the invention enables control of cone tilt angle and thereby control of the brightness characteristics of liquid crystal display devices. The process is especially useful for reducing cone tilt angle in mixtures of fluorine-containing, smectic or latent smectic liquid crystal compounds (preferably compounds having fluorinated terminal portions, such as those compounds disclosed, for example, in U.S. Pat. Nos. 4,886,619 (Janulis), 5,082,587 (janulis), 5,262,082 (Janulis et al.), 5,399,291 (Janulis et al.), and 5,437,812 (Janulis et al.) and in U.S. Ser. No. 08/338,957

(Janulis et al.) and U.S. Ser. No. 08/338,961 (Janulis et al.), as well as compounds having at least one chiral, fluorinated terminal portion). The compounds used in the process of the invention (in composition(s) (a)), unlike hydrocarbon liquid crystal compounds, in many cases show excellent compatibility with such fluorine-containing liquid crystal compounds, show a beneficial effect or only a minimal negative effect on the smectic C temperature range of the resulting mixtures (even when present at high concentrations), and provide tilted chiral smectic mixtures having low viscosity and fast electrical response times over broad temperature ranges. In addition, many of the compounds have broad smectic C temperature ranges, making them useful alone, as well as in admixture with other liquid crystal compounds (as dopants or as the major components), for electrooptical display applications.

In other aspects, this invention also provides fluorine-containing, smectic or latent smectic liquid crystal compounds useful in the process of the invention; mixtures comprising the compounds; mixtures prepared by the process of the invention; and electrooptical display devices containing the compounds or the mixtures.

DETAILED DESCRIPTION OF THE INVENTION

Compositions suitable for use (as composition(s) (a)) in the process of the invention are liquid crystal compositions which comprise at least one smectic or latent smectic liquid crystal compound comprising (i) an aliphatic fluorocarbon terminal portion comprising a terminal fluoroalkyl or fluoroether group and an alkylene group having at least two carbon atoms and containing at least one catenary ether oxygen atom, (ii) an aliphatic hydrocarbon terminal portion, and (iii) a central core connecting the terminal portions. Such smectic compounds exhibit surprisingly lower cone tilt angles and, in many cases, surprisingly broader smectic C mesophases than corresponding compounds which do not have such an alkylene group (having at least two carbon atoms and containing at least one catenary ether oxygen) in the aliphatic fluorocarbon terminal portion. The aliphatic fluorocarbon terminal portion of the compounds can be represented by the formula —D—$R_h$—$R_f$, where $R_h$ is an alkylene group having at least two carbon atoms and containing at least one catenary ether oxygen atom; $R_f$ is fluoroalkyl (preferably, perfluoroalkyl) or fluoroether (preferably, perfluoroether); and D is non-directionally selected from the group consisting of a covalent bond, —C(=O)O—$C_rH_{2r}$—, —O—$C_rH_{2r}$—, —O—($C_sH_{2s}$O—$)_tC_rH_{2r}$—, —$C_rH_{2r}$—, —($C_sH_{2s}$O—$)_tC_rH_{2r}$—, —OSO$_2$—, —SO$_2$—, —SO$_2$—$C_rH_{2r}$—,

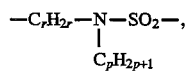

—C≡C—, —CH=CH—, —C(=O)—, —O(O=)C=$C_rH_{2r}$—,

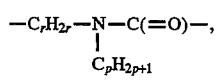

—CH=N—, —O—, —S—, —N($C_pH_{2p+1}$)—, and combinations thereof, where r and r' are independently integers of 0 to about 20, s is independently an integer of 1 to about 10 for each ($C_sH_{2s}$O), t is an integer of 1 to about 6, and p is an integer of 0 to about 4. When the $R_f$ group of the fluorocarbon terminal portion is perfluoroalkyl or perfluoroether, it can contain small amounts of residual carbon-bonded hydrogen atoms but is preferably completely fluorinated. Preferably, $R_f$ is perfluoroalkyl or perfluoroether (more preferably, perfluoroether) and contains from 1 to about 20 carbon atoms (more preferably, from about 4 to about 12 carbon atoms). $R_h$ preferably contains from 2 to about 12 carbon atoms (more preferably, from 2 to about 8). D is preferably selected from the group consisting of —O—, —C(=O)—, a covalent bond, and combinations thereof; more preferably, D is —O—.

The central core of the compounds generally comprises at least one or two rings independently selected from the group consisting of aromatic, heteroaromatic, alicyclic, substituted aromatic, substituted heteroaromatic, and substituted alicyclic rings, the rings being connected one with another by a covalent bond or by chemical groups selected from the group consisting of —COO—, —COS—, —HC=N—, —CH=CH—, —C≡C—, and —COSe—. The rings can be fused or non-fused. The heteroatoms within the heteroaromatic rings comprise at least one atom selected from the group consisting of nitrogen, oxygen, and sulfur. Non-adjacent ring carbon atoms in the alicyclic rings can be substituted by nitrogen, oxygen, or sulfur atoms.

A class of liquid crystal compounds which can be utilized (e.g., in composition(s) (a)) in the process of the present invention can be represented by the general formula I:

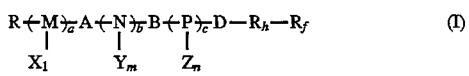

where M, N, and P are each independently selected from the group consisting of

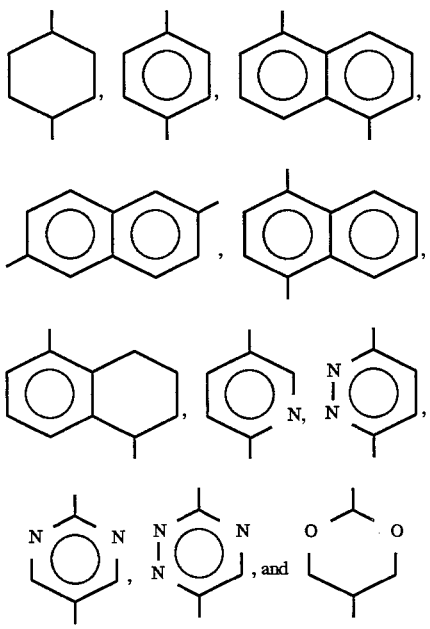

-continued

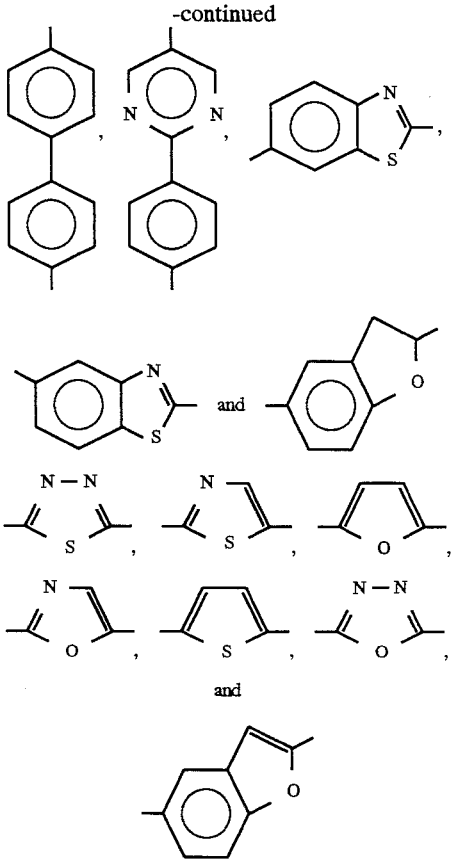

a, b, and c are each independently zero or an integer of from 1 to 3, with the proviso that the sum of a+b+c be at least 1;

each A and B are non-directionally and independently selected from the group consisting of a covalent bond, —C(=O)—O—, —C(=O)—S—, —(=O)—Se—, —C(=O)—Te—, —(CH$_2$CH$_2$)$_k$— where k is 1 to 4, —CH=CH—, —C≡C—, —CH=N—, —CH$_2$—O—, —C(=O)—, and —O—;

each X, Y, and Z are independently selected from the group consisting of —H, —Cl, —F, —Br, —I, —OH, —OCH$_3$, —CH$_3$, —CF$_3$, —OCF$_3$, —CN, and —NO$_2$;

each l, m, and n are independently zero or an integer of 1 to 4;

D is non-directionally selected from the group consisting of a covalent bond, —C(=O)—O—C$_r$H$_{2r}$—, —O—C$_r$H$_{2r}$—, —O—(O=)C—C$_r$H$_{2r}$—, —C≡C—, —CH=CH—, —C(=O)—, —O—(C$_s$H$_{2s}$O)$_t$C$_r$H$_{2r}$—, —C$_r$H$_{2r}$—, —(C$_s$H$_{2s}$O)$_t$C$_r$H$_{2r}$—, —O—, —S—, —OSO$_2$—, —SO$_2$—, —SO$_2$—C$_r$H$_{2r}$—,

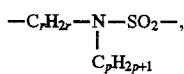

—N(C$_p$H$_{2p+1}$)—,

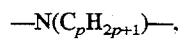

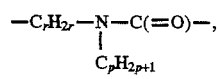

—CH=N—, and combinations thereof, where r and r' are independently integers of 0 to about 20, s is independently an integer of 1 to about 10 for each (C$_s$H$_{2s}$O), t is an integer of 1 to about 6, and p is an integer of 0 to about 4;

R is selected from the group consisting of —O—(C$_{q'}$H$_{2q'-v'}$—(R')$_{v'}$)—O)$_w$—C$_q$H$_{2q+1-v}$—(R')$_v$, —((C$_{q'}$H$_{2q'-v'}$—(R')$_{v'}$)—O)$_w$—C$_q$H$_{2q+1-v}$—(R')$_v$, —C(=O)—O—C$_q$H$_{2q+1-v}$—(R')$_v$, —O—(O=)C—C$_q$H$_{2q+1-v}$—(R')$_v$,

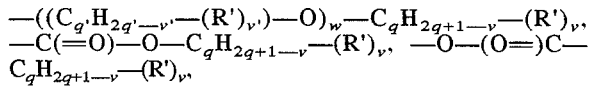

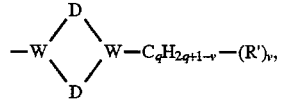

—CR'H—(D)$_g$—CR'H—C$_q$H$_{2q+1-v}$—(R')$_v$, where each R' is independently selected from the group consisting of —Cl, —F, —CF$_3$, NO$_2$, —CN, —H, —C$_q$H$_{2q+1}$, —O—(O=)C—C$_q$H$_{2q+1}$, —C(=L)—O—C$_q$H$_{2q+1}$, —Br, —OH, and —OC$_q$H$_{2q+1}$ (preferably, —H or —F); q' is independently an integer of 1 to about 20 for each (C$_{q'}$H$_{2q'}$—O); q is an integer of 1 to about 20; w is an integer of 0 to about 10; v is an integer of 0 to about 6; each v' is independently an integer of 0 to about 6; g is an integer of 1 to about 3; each D is independently and non-directionally selected from the group set forth for D above, with the proviso that the ring containing D has from about 3 to about 10 ring atoms; each W is independently selected from the group consisting of N, CR', and SIR';

R$_h$ is an alkylene group having at least two carbon atoms (preferably, from 2 to about 12 carbon atoms; more preferably, from 2 to about 8) and containing at least one catenary ether oxygen atom; and R$_f$ is fluoroalkyl or fluoroether (preferably, perfluoroalkyl or perfluoroether; more preferably, perfluoroether) and preferably contains from 1 to about 20 carbon atoms (more preferably, from about 4 to about 12 carbon atoms).

Particularly preferred R$_h$ moieties Can be represented by the general formula —(C$_s$H$_{2s}$O)$_t$C$_r$H$_{2r}$—, wherein s is independently an integer of 1 to about 10 for each (C$_s$H$_{2s}$O) (preferably, about 2 to about 7), t is an integer of 1 to about 6 (preferably, 1 to about 3), and r' is an integer of 1 to about 10 (preferably, 1).

In defining R$_f$, particularly preferred fluoroalkyl groups are those Which can be represented by the formula —C$_q$F$_{2q}$X', where q is as defined above (and, preferably, is at least about 3) and X' is hydrogen or fluorine. Other useful fluoroalkyl and fluoroether groups are those which can be represented by the formula —R$_f'$—R$_h'$, where R$_f'$ is a linear or branched, perfluorinated or partially-fluorinated alkylene group having from 1 to about 10 (preferably, from about 2 to about 6) carbon atoms and optionally containing one or more catenary, i.e., in-chain, ether oxygen atoms, and R$_h'$ is a linear or branched alkyl group having from 1 to about 14 (preferably, from about 3 to about 10) carbon atoms and optionally containing one or more catenary ether oxygen atoms. Preferably, R$_f'$ is perfluorinated, both R$_h'$ and R$_f'$ are linear, and at least one of the groups R$_h'$ and R$_f'$ contains at least one catenary ether oxygen atom. More preferably, R$_h'$ or both R$_h'$ and R$_f'$ contains at least one catenary ether oxygen atom. More preferably, R$_h'$ or both R$_h'$ contains at least one catenary ether oxygen atom.

Particularly preferred perfluoroether groups are those which can be represented by the formula —(C$_x$F$_{2x}$O)$_z$C$_y$F$_{2y+1}$, where x is independently an integer of 1 to about 10 for each (C$_x$F$_{2x}$O), y is an integer of 1 about 10, and z is an integer of 1 to about 10. Preferably, the perfluoroether group is linear, x is independently an integer of 1 to about 8 for each (C$_x$F$_{2x}$O), y is an integer of 1 to about 6, and z is an integer of 1 to about 6.

Many of the perfluoroether group-containing liquid crystal compounds used in the process of the invention when used alone or when mixed with each other or with other fluorine-containing liquid crystal compounds (preferably, the perfluoroether group-containing liquid crystal compounds described in U.S. Pat. Nos. 5,262,082 (Janulis et al.) and 5,437,812 (janulis et al.) and in U.S. Ser. No. 08/338,957 (Janulis et al.) and U.S. Ser. No. 08/338,961 (Janulis et al.), the descriptions of which are incorporated herein by reference) exhibit a reduced temperature dependence of the smectic interlayer spacing. This property provides for the spontaneous generation of a bookshelf type layer structure, which is ideal for a tilted chiral smectic liquid crystal device.

A preferred subclass of liquid crystal compounds for use in the process of the invention (e.g., in composition(s) (a)) are those compounds which can be represented by formula I, supra, wherein $R_f$ is fluoroether (preferably, perfluoroether) and $R_h$ is represented by the directional general formula $-(C_sH_{2s}O)_t-C_{r'}H_{2r'}-$, wherein s is independently an integer of 2 to about 10 (preferably, 3 to about 10; more preferably, 3 to about 7) for each $(C_sH_{2s}O)$, t is an integer of 1 to about 6 (preferably, 1 to about 3; more preferably, 1 to 2), and r' is an integer of 1 to about 10 (preferably, 1 to about 5; more preferably, 1); with the proviso that the compounds exhibit at least one tilted smectic mesophase. Preferably, $R_h$ has from about 3 to about 12 carbon atoms (more preferably from about 4 to about 8).

Another preferred subclass of liquid crystal compounds for use in the process of the invention (e.g., in composition (s) (a)) are those compounds which can be represented by formula I, supra, wherein $R_f$ is fluoroether (preferably, perfluoroether) and $R_h$ is represented by the directional general formula $-(C_sH_{2s}O)_t-C_{r'}H_{2r'}-$, wherein s is independently an integer of 3 to about 10 (preferably, 3 to about 7) for each $(C_sH_{2s}O)$, t is an integer of 1 to about 6 (preferably, 1 to about 3; more preferably, 1 to 2), and r' is an integer of 1 to about 10 (preferably, 1 to about 5; more preferably, 1); with the proviso that the compounds do not exhibit at least one tilted smectic mesophase. Preferably, $R_h$ has from about 4 to about 12 carbon atoms (more preferably from about 4 to about 8).

Such preferred compounds, in general, have enhanced smectic mesophases and low cone tilt angles (relative to the corresponding compounds which do not contain an extended hydrocarbon ether group adjacent to a terminal fluoroalkyl or fluoroether group) making them useful alone, as well as in admixture with other liquid crystal compounds (as dopants or as the major components), for electrooptical display applications. Mixtures of the compounds with other liquid crystal materials can be formulated to provide desired transition temperatures, broad mesophase temperature ranges, and reduced Cone tilt angles.

The fluorine-containing liquid crystal compounds useful in carrying out the process of the invention can be prepared by a process comprising the steps of (a) mixing at least one compound represented by the formula

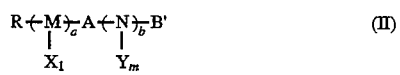

with at least one compound represented by the formula

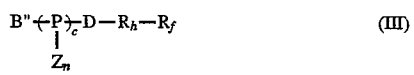

or mixing at least one compound represented by the formula

with at least one compound represented by the formula

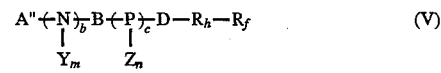

where M, N, P, a, b, c, A, B, X, Y, Z, l, m, n, D, R, $R_h$, and $R_f$ are as defined above for formula I; and each A', A", B', and B" are independently selected from the group consisting of —H, —Cl, —Br, —I, —OH, —COOH, —CH(CH$_2$OH)$_2$, —SH, —SeH, —TeH, —NH$_2$, —COCl, —CHO, —OSO$_2$R$_{f''}$ —OSO$_2$CH$_3$, —NH(C═O)OC$_q$H$_{2q+1}$, —NCO, —OSO$_2$-cyclo(C$_6$H$_4$)—CH$_3$, —CH$_2$COOH, and —CH(C(O)O-C$_q$H$_{2q+1}$)$_2$, where $R_{f''}$ is a perfluoroalkyl group having from 1 to about 10 carbon atoms and q is an integer of 0 to about 20, and with the proviso that A' can enter into an addition or condensation reaction with A" and that B' can enter into an addition or condensation reaction with B";

and (b) allowing compounds II and III or compounds IV and V to react, optionally in the presence of suitable coupling agent(s), i.e., reagent(s) which effect coupling.

Liquid crystal compositions suitable for use (as composition(s) (b)) in admixture with the above-described liquid crystal compositions (i.e., composition(s) (a)) are those liquid crystal compositions which comprise at least one smectic or latent smectic liquid crystal compound. At least one of compositions (a) and (b) must possess optical activity in order for the resulting combination to exhibit a cone tilt angle. Especially suitable compounds for use in composition(s) (b) are fluorine-containing, smectic or latent smectic liquid crystal compounds (preferably compounds having fluorinated terminal portions such as those compounds described, for example, in U.S. Pat. Nos. 4,886,619 (Janulis), 5,082,587 (Janulis), 5,262,082 (Janulis et al.), 5,399,291 (Janulis et al. ), and 5,437,812 (Janulis et al.) and in U.S. Ser. No. 08/338,957 (Janulis et al.) and U.S. Ser. No. 08/338,961 (Janulis et al.), the descriptions of which are incorporated herein by reference, as well as compounds having at least one chiral, fluorinated terminal portion).

The process of the invention can be carried out by combining composition(s) (a) and composition(s) (b). The combining or mixing of the compositions can be effected by introducing the compositions to a vessel, generally with simultaneous and/or subsequent agitation or stirring, e.g., roller mixing. The vessel can be either an open or a closed vessel of a size which is sufficient to hold both compositions while allowing room for mixing. The compositions can be formed prior to combination with each other, or, alternatively, one or more of the components of either can be combined with one or more of the components of the other prior to addition of the remaining components. Any order and manner of combination of the components of the compositions is acceptable. The resulting combination is preferably agitated or stirred sufficiently that a homogeneous mixture is achieved. This is preferably facilitated by applying sufficient heat to melt the combination or by dissolving the combination in a solvent, e.g., a polar aprotic solvent, with subsequent solvent removal, e.g., by evaporation.

The liquid crystal compounds to be utilized in the process can be selected based upon the magnitudes of their cone tilt angles (or, in the case of latent smectic liquid crystal compounds, the magnitudes of the cone tilt angle of mixtures containing the latent compound(s)), which can be determined by using a polarizing microscope equipped with a hot stage, as described below in the Examples. In general, composition (b) (generally having a greater cone tilt angle) can be combined with composition (a) (generally having a smaller cone tilt angle) to obtain a combination having a desired intermediate cone tilt angle. Preferably, composition (s) (a) are utilized in amount(s) such that the resulting combination has a cone tilt angle between about 10 and about 35 degrees (more preferably, between about 18 and about 26 degrees; most preferably, between about 18 and about 23 degrees). However, in some cases a cone tilt angle outside of these ranges may be desirable for a particular purpose and can be achieved by the mixing of compositions (a) and (b). Net cone tilt angles within these ranges can generally be achieved through an iterative process of combining compositions (a) and (b) in varying ratios and measuring the net cone tilt angles of the resulting combinations.

Objects and advantages of this invention are further illustrated by the following examples, but the particular materials and amounts thereof recited in these examples, as well as other conditions and details, should not be construed to unduly limit this invention.

In the following examples, all temperatures are in degrees Celsius and all parts and percentages are by weight unless indicated otherwise. Commercially available materials were chemically transformed by reaction pathways well-known to those skilled in the art and detailed in the examples. Chemical transformations were comprised of acylation, esterification, etherification, alkylation, and combinations thereof using fluorine-containing and non-fluorine-containing reactants to provide the precursor compounds, which, in turn, were allowed to react together to yield the fluorine-containing liquid crystal compounds used in the process of the invention.

Liquid crystal compounds prepared as described below were characterized by their melting or boiling points, and their structures were confirmed using at least one of the following methods of analysis: high pressure liquid chromatography (HPLC); $^{13}C$, $^{1}H$, and $^{19}F$ nuclear magnetic resonance (NMR); and infrared and mass spectroscopies.

EXAMPLES

The 5-alkyl-2-(4-hydroxyphenyl) pyrimidines used in the examples were prepared essentially as described by Zaschke and Stolle in "Synthese niedrigschmelzender Kristallin-Flussiger Heterocyclen; 5-n-Alkyl-2-[4-n-alkanoyloxy-phenyl]pyrimidine," Z.Chem. 15, 441–3 (1975). (S)- and (R)-2-fluoro-decyl-p-toluenesulfonate were prepared essentially as described by Nobira et al. in Mol. Cryst. Liq. Cryst. 180B, 379 (1990). Fluorinated alcohols were prepared essentially as described in U.S. Pat. No. 5,262,082 (Janulis et al.; the description of which is incorporated herein by reference) by sodium borohydride reduction of the corresponding perfluorinated acids (or derivatives), which had been prepared by electrochemical fluorination (ECF) or by direct fluorination (using elemental fluorine) of the corresponding hydrocarbon acids (or derivatives). See, e.g., the description of ECF given in U.S. Pat. No. 2,519,983 (Simons), the description of which is incorporated herein by reference. Direct fluorination is described, e.g., in U.S. Pat. No. 5,362,919 (Costello et al.), the description of which is also incorporated herein by reference.

Examples 1–39 describe procedures for preparing liquid crystal compounds which can be used in the process of this invention. (The compounds of Examples 1–37 are liquid crystal compounds of the invention.) The chemical structure of each compound is given in Table 1.

Example 1

Preparation of 5-Octyl-2-(4-(2-(2-(nonafluorobutoxy)tetrafluoroethoxy)-2,2-difluoroethoxy)butoxy)phenyl)pyrimidine A 500 mL flask was charged with 4-(2-(2-(nonafluorobutoxy)tetrafluoroethoxy)-2,2-difluoroethoxy)-1-bromobutane (21.9 g, 38.5 mmol; prepared from 1,4-dibromobutane and 2-(2-(nonafluorobutoxy)tetrafluoroethoxy)-2,2-difluoroethanol), 5-octyl-2-(4-hydroxyphenyl)pyrimidine (10 g, 35 mmol), potassium carbonate (5.4 g, 39 mmol), and acetonitrile (200 mL), and the resulting mixture was stirred and refluxed overnight under nitrogen. Toluene (150 mL) and water (150 mL) were added to the refluxed mixture. The resulting toluene layer was collected and residual water removed by distillation using a Dean-Stark apparatus. The toluene layer was then filtered through a pad of silica gel and the toluene removed under reduced pressure. The crude product was further purified by distillation using a Kugelrohr apparatus (b.p. 210°–15° C. at 0.1 torr). The resulting yield was 14.4 g.

Example 2

Preparation of 5-Octyl-2-(5-(2-(2-(nonafluorobutoxy)tetrafluoroethoxy)-2,2-difluoroethoxy)pentyloxy)phenyl)pyrimidine The title compound was prepared essentially as in Example 1 by combining 5-(2-(2-(nonafluorobutoxy)tetrafluoroethoxy)-2,2-difluoroethoxy)pentyl bromide (23.5 g, 38.5 mmol; prepared from 1,5-dibromopentane and 2-(2-(nonafluorobutoxy)tetrafluoroethoxy)-2,2-difluoroethanol) with 5-octyl-2-(4-hydroxyphenyl)pyrimidine (10 g, 35 mmol). A yield of 19.8 g was obtained (b.p. 200°–10° C. at 0.4 torr).

Example 3

Preparation of 5-Octyl-2-(3-(2-(2-(nonafluorobutoxy)tetrafluoroethoxy)-2,2-difluoroethoxy)propoxy)phenyl)pyrimidine The title compound was prepared essentially as in Example 1 by combining 3-(2-(2-(nonafluorobutoxy)tetrafluoroethoxy)-2,2-difluoroethoxy)propyl bromide (14.8 g, 26.8 mmol; prepared by combining 1, 3-dibromopropane and 2-(2-(nonafluorobutoxy)tetrafluoroethoxy)-2,2-difluoroethanol) with 5-octyl-2-(4-hydroxyphenyl) pyrimidine (7.3 g, 26.8 mmol). After refluxing for 7 hours, toluene and water were added to the resulting mixture, and the resulting organic phase was extracted with three 30 mL aliquots of brine and then dried over anhydrous $MgSO_4$. The organic phase was then filtered, the solvent was removed under reduced pressure, and the resulting material was dissolved in 5 volume percent ethyl acetate/hexane. The resulting hexane/ethyl acetate solution was purified by flash chromatography on silica gel, and the solvent mixture was removed under reduced pressure. The resulting product was further purified by distillation using a Kugelrohr apparatus to provide a yield of 14.5 g.

Example 4

Preparation of 5-Octyl-2-[4-(6-(2-(2-(nonafluorobutoxy)tetrafluoroethoxy)-2,2-difluoroethoxy)hexyloxy)phenyl]pyrimidine The title compound was prepared essentially as in Example 1 by combining 5-octyl-2-(4-hydroxyphenyl) pyrimidine (1.01 g, 3.55 mmol) and 6-(2-(2-(nonafluorobutoxy)tetrafluoroethoxy)-2,2-difluoroethoxy)-1-bromohexane (2.4 g, 4.03 mmol; prepared by combining 1,6-dibromohexane and 2-(2-(nonafluorobutoxy)tetrafluoroethoxy)-2,2-difluoroethanol). The resulting crude product was isolated and further purified essentially as described in Example 3, eluting with 1 vol. % ethyl acetate/toluene

Example 5

Preparation of 5-Hexyloxy-2-[4-(5-(2-(2-(nonafluorobutoxy)tetrafluoroethoxy)-2,2-difluoroethoxy)pentyloxy)phenyl]pyrimidine The title compound was prepared essentially as in Example 1 by combining 5-hexyloxy-2-(4-hydroxyphenyl) pyrimidine (8.0 g, 29.4 mmol) and 5-(2-(2-(nonafluorobutoxy)tetrafluoroethoxy)-2,2-difluoroethoxy)-1-bromopentane (18.6 g, 32 mmol, Example 2). The resulting crude product was isolated and further purified essentially as described in Example 1 (b.p. 210°–25° C. at 0.3 torr).

Example 6

Preparation of 5-Heptyloxy-2-[4-(3-(2-(2-(nonafluorobutoxy)tetrafluoroethoxy)-2,2-difluoroethoxy)propoxy)phenyl]pyrimidine The title compound was prepared essentially as described in Example 1 by combining 5-heptyloxy-2-(4-hydroxyphenyl)pyrimidine (3.0 g, 10.0 mmol) and 3-(2-(2-(nonafluorobutoxy) tetrafluoroethoxy)-2,2-difluoroethoxy)-1-bromopropane (6.6 g, 12.0 mmol, Example 10). The product was isolated by addition of water (60 mL) to the resulting mixture, followed by filtration and recrystallization from ethanol. The recrystallized precipitate was dried at about 130° C., and the resulting product was further purified by Kugelrohr distillation (b.p. 180°–190° C. at 2 torr; yield 5.6 g).

Example 7

Preparation of 5-Hexyloxy-2- [4-(7-(2-(2-(nonafluorobutoxy) tetrafluoroethoxy)-2,2-difluoroethoxy)heptyloxy)phenyl]pyrimidine The title compound was prepared essentially as described in Example 1 by combining 5-hexyloxy-2-(4-hydroxyphenyl)pyrimidine (3.0 g, 11.0 mmol) and 7-(2-(2-(nonafluorobutoxy) tetrafluoroethoxy)-2,2-difluoroethoxy)-1-bromoheptane (7.7 g, 12.0 mmol; prepared by combining 1,7-dibromoheptane with 2-( 2-(nonafluorobutoxy) tetrafluoroethoxy)-2,2-difluoroethanol). Product was isolated by addition of water (50 mL) to the resulting mixture, followed by filtration and recrystallization from ethanol. The recrystallized precipitate was dried at about 130° C., and the resulting product was further purified by Kugelrohr distillation (b.p. 210°–222° C. at 0.03 torr; yield 7.3 g).

Example 8

Preparation of 5-Octyl-2-[4-(4-(5-(2-(nonafluorobutoxy)tetrafluoroethoxy)-2,2,3,3,4,4,5,5-octafluoropentoxy)butoxy)phenyl]pyrimidine The title compound was prepared essentially as in Example 1 by combining 5-octyl-2-(4-hydroxyphenyl) pyrimidine (1.0 g, 3.52 mmol) and 6-(5-(2-(nonafluorobutoxy)tetrafluoroethoxy)-2,2,3,3,4,4,5,5,-octafluoropentyloxy)-1-bromobutane (3.07 g, 4.0 mmol; prepared by combining 1,4-dibromobutane and 2-(2-(nonafluorobutoxy)tetrafluoroethoxy)-2,2,3,3,4,4,5,5-octafluoropentanol). The resulting crude product was isolated and further purified essentially as described in Example 3, eluting with 20 volume percent ethyl acetate/cyclohexane, to yield 2.53 g of purified product.

Example 9

Preparation of 5-Octyl-2-[4-(2-(6-(2-(nonafluorobutoxy) tetrafluoroethoxy)-2,2,3,3,4,4,5,5,6,6-decafluorohexyloxy)ethoxy)phenyl]pyrimidine The title compound was prepared essentially as in Example 1 by combining 5-octyl-2-(4-hydroxyphenyl) pyrimidine (1.04 g, 3.64 mmol) and 2-(6-(2-(nonafluorobutoxy)tetrafluoroethoxy)-2,2,3,3,4,4,5,5,6,6-decafluorohexyloxy)-1-p-toluenesulfonyl ethane (3.36 g, 4.05 mmol; prepared by combining ethylene carbonate and 6-(2-(nonafluorobutoxy)tetrafluoroethoxy)-2,2,3,3,4,4,5,5,6,6-decafluorohexanol and then preparing the p-toluenesulfonate from p-toluenesulfonyl chloride. The resulting crude product was isolated and further purified essentially as described in Example 3, eluting with ethyl acetate/hexane, to yield 2.88 g of purified product.

Example 10

Preparation of 5-Octyl-2-[4-(3-(6-(2-(nonafluorobutoxy)tetrafluoroethoxy)-2,2,3,3,4,4,5,5,6,6-dodecafluorohexyloxy)propoxy)phenyl] pyrimidine The title compound was prepared essentially as in Example 1 by combining 5-octyl-2-(4-hydroxyphenyl) pyrimidine (1 g, 3.51 mmol) and 3-(6-(2-(nonafluorobutoxy)tetrafluoroethoxy)-2,2,3,3,4,4,5,5,6,6-decafluorohexyloxy)-1-bromopropane (3.04 g, 4.04 mmol; prepared by combining 1,3-dibromopropane and 2-(2-(nonafluorobutoxy)tetrafluoroethoxy)- 2,2,3,3,4,4,5,5,6,6-decafluorohexanol). The resulting crude product was isolated and further purified essentially as described in Example 3, eluting with 2 volume percent ethyl acetate/toluene, to yield 2.68 g of purified product.

Example 11

Preparation of 5-Octyl-2-[4-(4-(6-(2-(nonafluorobutoxy)tetrafluoroethoxy)-2,2,3,3,4,4,5,5,6,6-decafluorohexyloxy)butoxy)phenyl]pyrimidine The title compound was prepared essentially as in Example 1 by combining 5-octyl-2-(4-hydroxyphenyl) pyrimidine (1.01 g, 3.56 mmol) and 4-(6-(2-(nonafluorobutoxy)tetrafluoroethoxy)-2,2,3,3,4,4,5,5,6,6-decafluorohexyloxy)-1-bromobutane (3.07 g, 4.0 mmol; prepared by combining 1,4-dibromobutane and 2-(2-(nonafluorobutoxy)tetrafluoroethoxy)-2,2,3,3,4,4,5,5,6,6-decafluorohexanol). The resulting crude product was isolated and further purified essentially as described in Example 3, eluting with 15 volume percent ethyl acetate/hexane, to yield 2.3 g of purified product.

Example 12

Preparation of 5-(2-(Ethoxy)ethoxy)-2-[4-(3-(2-(2-(nonafluorobutoxy) tetrafluoroethoxy)-2,2-difluoroethoxy)propoxy)phenyl]pyrimidine A 500 mL flask was charged with 5-benzyl-2-[4-hydroxyphenyl]pyrimidine (10.0 g, 40 mmol), 3-(2-(2-(nonafluorobutoxy)tetrafluoroethoxy)-2,2-difluoroethoxy)-1-bromopropane (24.2 g, 44 mmol, Example 3), potassium carbonate (6.1 g, 44 mmol), and anhydrous acetonitrile (100 mL), and the resulting mixture was stirred overnight at 85° C. under nitrogen. Water (150 mL) was added and the mixture was cooled to 5° C. and then filtered and dried to produce 5-benzyloxy-2-[4-(3-(2-(2-(nonafluorobutoxy) tetrafluoroethoxy)-2,2-difluoroethoxy)propoxy)phenyl] pyrimidine. This intermediate was further purified by recrystallization from acetone, and the benzyl protecting group was removed by hydrogenation using Pd/C catalyst.

The title compound was prepared essentially as in Example 1 by combining 5-hydroxy-2-[4-(3-(2-(2-

(nonafluorobutoxy)tetrafluoroethoxy)-2,2-difluoroethoxy) propoxy)phenyl]pyrimidine (1.0 g, 1.51 mmol,) and 2-bromoethyl ethyl ether (0.58 g, 3.79 mmol). The resulting crude product was isolated and further purified essentially as described in Example 3, eluting with 30 volume percent ethyl acetate/hexane, to yield 0.76 g of purified product.

Example 13

Preparation of 5-(2-(2-(Butoxy)ethoxy)ethoxy)-2-[4-(3-(2-(2-(nonafluorobutoxy)tetrafluoroethoxy)-2,2-difluoroethoxy)propoxy)phenyl]pyrimidine The title compound was prepared essentially as in Example 1 by combining 5-hydroxy-2-[4-(3-(2-(2-(nonafluorobutoxy)tetrafluoroethoxy)-2,2-difluoroethoxy) propoxy)phenyl]pyrimidine (1.22 g, 1.85 mmol, Example 10) and 1-bromo-2-(2-butoxyethoxy) ethane (0.81 g, 3.62 mmol). The resulting crude product was isolated and further purified essentially as described in Example 3, eluting with 30 volume percent ethyl acetate/hexane, to yield 1.13 g of purified product.

Example 14

Preparation of 5-(2-(S)fluorooctyloxy)-2-[4-(3-(2-(2-(nonafluorobutoxy)tetrafluoroethoxy)-2,2-difluoroethoxy)propoxy)phenyl]pyrimidine The title compound was prepared essentially as in Example 1 by combining 5-hydroxy-2-[4-(3-(2-(2-(nonafluorobutoxy)tetrafluoroethoxy)-2,2-difluoroethoxy) propoxy)phenyl]pyrimidine (5.9 g, 8.9 mmol, Example 12) and 2-(R)-fluorooctyl-1-p-toluenesulfonate (2.75 g, 9.5 mmol; which can be prepared as described by Nohira et al. in Mol. Cryst. Liq. Cryst. 180B, 379 (1990)). The resulting crude product was isolated and further purified by recrystallization from ethanol to provide a yield of 5.3 g.

Example 15

Preparation of 5-Hexyloxy-2-[4-(2-(2-(2-(2-(nonafluorobutoxy)tetrafluoroethoxy)-2,2-difluoroethoxy)ethoxy)ethoxy)phenyl]pyrimidine The title compound was prepared essentially as in Example 1 by combining 2-(2-(2-(2-(nonafluorobutoxy) tetrafluoroethoxy)-2,2-difluoroethoxy)ethoxy)ethyl bromide (7.7 g of 90% purity by gas chromatography 11.8 mmol) with 5-hexyloxy-2-(4-hydroxyphenyl)pyrimidine (3.0 g, 11.0 mmol). The resulting product was isolated by addition of water (50 mL) to the reaction mixture, followed by filtration and recrystallization from ethanol. The recrystallized precipitate was dried at about 130° C., and the resulting product was further purified by distillation using a Kugelrohr apparatus (b.p. 185°–210° C. at 0.01 torr; yield 5.6 g).

Example 16

Preparation of 5-Octyl-2-[4-(4-(4-(2-(nonafluorobutoxy)tetrafluoroethoxy)-2,2,3,3,4,4-hexafluorobutoxy)butoxy)phenyl]pyrimidine The title compound was prepared essentially as in Example I by combining 4-(4-(2-(nonafluorobutoxy) tetrafluoroethoxy)-2,2,3,3,4,4-hexafluorobutoxy)butyl bromide (25.6 g, 38.5 mmol; prepared by combining 1,4-dibromobutane and 2-(2-(nonafluorobutoxy) tetrafluoroethoxy)-2,2-difluoroethanol) with 5-octyl-2-(4-hydroxyphenyl)pyrimidine (10 g, 35 mmol). The resulting product was further purified by recrystallization from heptane, followed by Kugelrohr distillation (b.p. 200°–210° C. at 0.4 torr; yield of 20.4 g).

Example 17

Preparation of 5-Hexyloxy-2-[4-(3-(2-(2-(trifluoromethoxy)tetrafluoroethoxy)-2,2-difluoroethoxy)propoxy)phenyl]pyrimidine The title compound was prepared essentially as in Example 1 by combining 3-(2-(2-(trifluoromethoxy) tetrafluoroethoxy)-2,2-difluoroethoxy)-1-chloropropane (4.5 g, 11.7 mmol; prepared by combining 1-bromo-3-chloropropane with 3-(2-(2-(trifluoromethoxy) tetrafluoroethoxy)-2,2-difluoroethanol) with 5-hexyloxy-2-(4-hydroxyphenyl)pyrimidine (3.0 g, 11.0 mmol). The resulting product was isolated by addition of water (50 mL) to the reaction mixture, followed by filtration and recrystallization from ethanol. The recrystallized precipitate was dried at about 130° C., and the resulting product was further purified by distillation using a Kugelrohr apparatus (b.p. 180°–183° C. at 0.1 torr; yield of 3.9 g).

Example 18

Preparation of 5-Octyl-2-[4-(3-(2-(2-(pentafluoroethoxy) tetrafluoroethoxy)-2,2-difluoroethoxy)propoxy)phenyl]pyrimidine The title compound was prepared essentially as in Example 1 by combining 5-octyl-2-(4-hydroxyphenyl) pyrimidine (2.0 g, 7.3 mmol), 3-(2-(2-(pentafluoroethoxy) tetrafluoroethoxy)-2,2-difluoroethoxy)-1-bromopropane (3.38 g, 7.47 mmol; prepared by combining 1,3-dibromopropane with 3-(2-(2-(pentafluoroethoxy) tetrafluorooethoxy)- 2,2-difluoroethanol), and potassium carbonate (1.16 g, 8.43 mmol) in acetonitrile (20 mL) and refluxing the resulting mixture under nitrogen overnight. The mixture was cooled and filtered, and the resulting solids were washed with toluene (50 mL). The toluene was then removed under reduced pressure, and the resulting waxy solid was dissolved in toluene (50 mL) and washed with three 30 mL aliquots of perfluorohexane. After removing the toluene under reduced pressure, the resulting crude product was further purified by silica gel chromatography, eluting with 20 volume percent ethyl acetate/hexane, to yield 3.60 g of purified product.

Example 19

Preparation of 5-Octyl-2-[4-(4-(2-(2-(pentafluoroethoxy)tetrafluoroethoxy)2,2-difluoroethoxy)butoxy)phenyl]pyrimidine The title compound was prepared essentially as in Example 1 by combining 5-octyl-2-(4-hydroxyphenyl) pyrimidine (1,995 g, 7.01 mmol) and 4-(2-(2-(pentafluoroethoxy) tetrafluoroethoxy)-2,2-difluoroethoxy)-1-bromobutane (3.44 g, 7.36 mmol; prepared by combining 1,4-dibromobutane with 3-(2-(2-(pentafluoroethoxy) tetrafluoroethoxy)-2,2-difluoroethanol). The resulting crude product was isolated and further purified essentially as described in Example 3, eluting with 15 volume percent ethyl acetate/hexane, to yield 4.12 g of purified product.

Example 20

Preparation of 5-Hexyloxy-2-(3-(2-(2-(pentafluoroethoxy)tetrafluoroethoxy)-2,2-difluoroethoxy)propoxy)phenyl)pyrimidine The title compound was prepared essentially as in Example 1 by combining 3-(2-(2-(pentafluoroethoxy)

tetrafluoroethoxy)-2,2-difluoroethoxy)propyl bromide (5.3 g, 11.7 mmol, Example 18) with 5-hexyloxy-2-(4-hydroxyphenyl)pyrimidine (3.0 g, 11 mmol). The resulting crude product was further purified by Kugelrohr distillation (b.p. 185°–195° C. at 0.4 torr; yield of 4.1 g).

Example 21

Preparation of 5-Hexyloxy-2-[4-(4-(2-(2-(pentafluoroethoxy) tetrafluoroethoxy)-2,2-difluoroethoxy)butoxy)phenyl]pyrimidine The title compound was prepared essentially as in Example 1 by combining 4-(2-(2-(pentafluoroethoxy) tetrafluoroethoxy)-2,2-difluoroethoxy)-1-bromobutane (14.9 g, 32.0 mmol, Example 19) with 5-hexyloxy-2-(4-hydroxyphenyl)pyrimidine (8.0 g, 29.4 mmol). The resulting product was isolated by addition of water (160 mL), followed by filtration and recrystallization from ethanol. The recrystallized precipitate was dried at about 130° C., and the resulting product was further purified by distillation using a Kugelrohr apparatus (b.p. 190°–205° C. at 0.3 torr; yield of 15.2 g).

Example 22

Preparation of 5-Hexyloxy-2-[4-(5-(2-(2-(pentafluoroethoxy)tetrafluoroethoxy)-2,2-difluoroethoxy)pentyloxy)phenyl]pyrimidine The title compound was prepared essentially as in Example 1 by combining 5-hexyloxy-2-(4-hydroxyphenyl) pyrimidine (2.26 g, 8.3 mmol) with 5-(2-(2-(pentafluoroethoxy) tetrafluoroethoxy)-2,2-difluoroethoxy)-1-bromopentane (4.08 g, 8.3 mmol; prepared by combining 1,5-dibromopentane with 2-(2-(pentafluoroethoxy) tetrafluoroethoxy)-2,2-difluoroethanol). Product was isolated by addition of water (160 mL) to the resulting mixture, followed by filtration and recrystallization from ethanol. The recrystallized precipitate was dried at about 130° C., and the resulting product was further purified by Kugelrohr distillation (b.p. 190°–205° C. at 0.3 torr; yield of 15.2 g).

Example 23

Preparation of 5-(2-(2-(2-Methoxy (ethoxy)ethoxy) ethoxy))-2-[4-(4-(2-(2-(pentafluoroethoxy) tetrafluoroethoxy) 2,2-difluoroethoxy)butoxy) phenyl]pyrimidine The title compound was prepared essentially as in Example 12 by first combining 5-benzyl-2-[4-hydroxyphenyl]pyrimidine (5.0 g, 18 mmol) and 3-(2-(2-(pentafluoroethoxy)tetrafluoroethoxy)-2,2-difluoroethoxy)-1-bromobutane (10.3 g, 22 mmol, Example 19) to produce 5-benzyloxy-2-[4-(4-(2-(2-(pentafluoroethoxy) tetrafluoroethoxy)-2,2-difluoroethoxy)butoxy)phenyl] pyrimidine. This intermediate was further purified by recrystallization from acetone, and the benzyl protecting group was removed by hydrogenation using Pd/C catalyst.

The resulting 5-hydroxy-2-[4-(4-(2-(2-(pentafluoroethoxy)tetrafluoroethoxy)-2,2-difluoroethoxy) butoxy)phenyl]pyrimidine (1.0 g, 1.74 mmol) was combined with 2-(2-(2-methoxy(ethoxy)ethoxy)-1-chloroethane (0.38 g, 2.1 mmol) using essentially the procedure of Example 1, to provide a product yield of 0.99 g.

Example 24

Preparation of 5-Octyl-2-[4-(3-(2-(2-(2-(trifluoromethoxy)tetrafluoroethoxy) tetrafluoroethoxy)-2,2-difluoroethoxy)propoxy) phenyl]pyrimidine The title compound was prepared essentially as in Example 1 by combining 3-(2-(2-(2-(trifluoromethoxy) tetrafluoroethoxy)tetrafluoroethoxy)-2,2-difluoroethoxy) 1-chloropropane (18.3 g, 38.5 mmol; prepared from 1-bromo-3-chloropropane (107 g, 0.7 mol) and 2-(2-(2-(trifluoromethoxy)tetrafluoroethoxy)tetrafluoroethoxy)-2,2-difluoroethanol (125 g, 0.31 mol) essentially as in Example 2) with 5-octyl-2-(4-hydroxyphenyl) pyrimidine (10 g, 35 mmol). The crude product was further purified by Kugelrohr distillation (b.p. 200°–210° C. at 0.4 torr; yield of 10.0 g).

Example 25

Preparation of 5-Octyl-2-[4-(4-(2-(2-(2-(trifluoromethoxy)tetrafluoroethoxy) tetrafluoroethoxy)-2,2-difluoroethoxy)butoxy) phenyl]pyrimidine The title compound was prepared essentially as in Example 1 by combining 4-(2-(2-(2-(trifluoromethoxy) tetrafluoroethoxy)tetrafluoroethoxy)-2,2-difluoroethoxy) 1-bromobutane (20.9 g, 38.5 mol; prepared from 1,4-dibromobutane and 2-(2-(2-(trifluoromethoxy) tetrafluoroethoxy)tetrafluoroethoxy)-2,2-difluoroethanol) with 5-octyl-2-(4-hydroxyphenyl)pyrimidine (10.0 g, 0.35 mol). The resulting product was further purified by recrystallization from ethanol and subsequent Kugelrohr distillation to provide a yield of 17.5 g (b.p. 195°–220° C. at 0.1 torr).

Example 26

Preparation of 5-Octyl-2-[4-(5-(2-(2-(2-(trifluoromethoxy)tetrafluoroethoxy) tetrafluoroethoxy)-2,2-difluoroethoxy)pentyloxy) phenyl]pyrimidine The title compound was prepared essentially as in Example 1 by combining 5-(2-(2-(2-(trifluoromethoxy) tetrafluoroethoxy)tetrafluoroethoxy)-2,2-difluoroethoxy)1-bromopentane (18.3 g, 38.5 mmol; prepared from 1,5-dibromopentane (107 g, 0.7 mol) and 2-(2-(2-(trifluoromethoxy)tetrafluoroethoxy)tetrafluoroethoxy)-2,2-difluoroethanol (125 g, 0.31 mol) essentially as in Example 2 ) with 5-octyl-2-(4-hydroxyphenyl)pyrimidine (10 g, 35 mmol) to provide product boiling at 200°–210° C. at 0.4 torr (yield of 20.8 g).

Example 27

Preparation of 5-Octyl-2-[4-(6-(2-(2-(2-(trifluoromethoxy)tetrafluoroethoxy) tetrafluoroethoxy)-2,2-difluoroethoxy)hexyloxy) phenyl]pyrimidine The title compound was prepared essentially as in Example 1 by combining 6-(2-(2-(2-(trifluoromethoxy) tetrafluoroethoxy)tetrafluoroethoxy)-2,2-difluoroethoxy)-1-bromohexane (85 g, 0.155 mol; prepared from 1,6-dibromohexane (500 g, 0.7 mol), 10 2-(2-(2-(trifluoromethoxy)tetrafluoroethoxy)tetrafluoroethoxy)-2,2-difluoroethanol (150 g, 0.37 mol), and potassium t-butoxide (412 mL of 1M solution in t-butanol)) with 5-octyl-2-(4-hydroxyphenyl)pyrimidine (45 g, 0. 162 mol). The crude product was further purified by recrystallization from heptane and subsequently dried in a vacuum oven (yield of 93.0 g).

Example 28

Preparation of 5-Hexyloxy-2-[4-(3-(2-(2-(2-(trifluoromethoxy)tetrafluoroethoxy) tetrafluoroethoxy)-2,2-difluoroethoxy)propoxy) phenyl]pyrimidine The title compound was prepared essentially as in Example 1 by combining 3-(2-(2-(2-(trifluoromethoxy)

tetrafluoroethoxy)tetrafluoroethoxy)-2,2-difluoroethoxy)-1-chloropropane (5.42 g, 11.4 mmol, Example 24) with 5-hexyloxy-2-(4-hydroxyphenyl)pyrimidine (3 g, 10.0 mmol). Product was isolated by addition of water (100 mL) to the resulting mixture, followed by filtration and recrystallization from ethanol. The recrystallized precipitate was dried at about 130° C., and the resulting product was further purified by Kugelrohr distillation (b.p. 170°–180° C. at 2.0 torr; yield of 5.4 g).

Example 29

Preparation of 5-pentyloxy-2-[4-(3-(2-(2-(2-(trifluoromethoxy)tetrafluoroethoxy)tetrafluoroethoxy)-2,2-difluoroethoxy)propoxy)phenyl]pyrimidine The title compound was prepared essentially as in Example 1 by combining 3-(2-(2-(2-(trifluoromethoxy)tetrafluoroethoxy)tetrafluoroethoxy)-2,2-difluoroethoxy)-1-chloropropane (6.1 g, 28.0 mmol, Example 24) with 5-pentyloxy-2-[4-hydroxyphenyl]pyrimidine (3 g, 11.6 mmol) in dimethylformamide and stirring at 120° C. overnight to provide product boiling at 185°–190° C. at 0.3 torr (yield of 5.5 g).

Example 30

Preparation of 5-Heptyloxy-2-[4-(3-(2-(2-(2-(trifluoromethoxy)tetrafluoroethoxy)tetrafluoroethoxy)-2,2-difluoroethoxy)propoxy)phenyl]pyrimidine The title compound was prepared essentially as in Example I by combining 3-(2-(2-(2-(trifluoromethoxy)tetrafluoroethoxy)tetrafluoroethoxy)-2,2-difluoroethoxy)-1-chloropropane (5.5 g, 15.0 mmol, Example 24) with 5-heptyloxy-2-(4-hydroxyphenyl)pyrimidine (3 g, 10.5 mmol) in dimethylformamide and stirring at 120° C. overnight to provide product boiling at 195°–210° C. at 0.3 torr (yield of 5.6 g).

Example 31

Preparation of 5-Octyloxy-2-[4-(3-(2-(2-(2-(trifluoromethoxy)tetrafluoroethoxy)tetrafluoroethoxy)-2,2-difluoroethoxy)propoxy)phenyl]pyrimidine The title compound was prepared essentially as in Example 1 by combining 3-(2-(2-(2-(trifluoromethoxy)tetrafluoroethoxy)tetrafluoroethoxy)-2,2-difluoroethoxy)-1-chloropropane (5.2 g, 10.9 mmol, Example 24) with 5-octyloxy-2-(4-hydroxyphenyl)pyrimidine (3 g, 10.0 mmol) in dimethylformamide and stirring at 120° C. overnight. The resulting product was further purified by Kugelrohr distillation (b.p. 195°–210° C. at 0.3 torr), followed by recrystallization from ethanol and additional distillation (yield of 3.5 g).

Example 32

Preparation of 5-Heptyloxy-2-[4-(4-(2-(2-(2-(trifluoromethoxy)tetrafluoroethoxy)tetrafluoroethoxy)-2,2-difluoroethoxy)butoxy)phenyl]pyrimidine The title compound was prepared essentially as in Example 1 by combining 4-(2-(2-(2-(trifluoromethoxy)tetrafluoroethoxy)tetrafluoroethoxy)-2,2-difluoroethoxy)-1-bromobutane (6.1 g, 15.0 mmol, Example 25) with 5-heptyloxy-2-(4-hydroxyphenyl)pyrimidine (3 g, 10.5 mmol). The resulting crude product was further purified by recrysallization from ethanol and subsequent Kugelrohr distillation (b.p. 200°–210° C. at 0.3 torr; yield of 5.2 g).

Example 33

Preparation of 5-Octyl-2-[4-(5-(2-(nonafluorobutoxy)-2,2-difluoroethoxy)pentyloxy)phenyl]pyrimidine The title compound was prepared essentially as in Example 1 by combining 5-octyl-2-(4-hydroxyphenyl)pyrimidine (6.0 g, 21 mmol) and 5-(2-(nonafluorobutoxy)-2,2-difluoroethoxy)-1-bromopentane (12 g, 23 mmol; prepared by combining 1,5-dibromopentane with 2-(nonafluorobutoxy)-2,2-difluoroethanol). After refluxing overnight, the resulting crude product was isolated by filtration and further purified by recrystallization from ethanol, followed by Kugelrohr distillation (b.p. 190°–200° C. at 0.1 torr; yield of 6.4 g).

Example 34

Preparation of 5-Octyl-2-[4-(6-(2-(nonafluorobutoxy)-2,2-difluoroethoxy)hexyloxy)phenyl]pyrimidine The title compound was prepared essentially as in Example 1 by combining 5-octyl-2-(4-hydroxyphenyl)pyrimidine (8.0 g, 28.13 mmol) and 6-(2-(nonafluorobutoxy)-2,2-difluoroethoxy)-1-bromohexane (14.15 g, 29.54 mmol; prepared by combining 1,6-dibromohexane with 2-(nonafluorobutoxy)-2,2-difluoroethanol). After refluxing overnight, the resulting crude product was isolated by filtration and further purified by recrystallization from ethanol, followed by Kugelrohr distillation (b.p. 200° C. at 0.25 torr).

Example 35

Preparation of 5-Octyl-2-[4-(4-(2-(2-(tridecafluorohexyloxy)tetrafluoroethoxy)-2,2-difluoroethoxy)butoxy)phenyl]pyrimidine The title compound was prepared essentially as in Example 1 by combining 5-octyl-2-(4-hydroxyphenyl)pyrimidine (1.03 g, 3.61 mmol) and 4-(2-(2-(tridecafluorohexyloxy)tetrafluoroethoxy)-2,2-difluoroethoxy)-1-bromobutane (2.68 g, 4.02 mmol; prepared from 1,4-dibromobutane and 2-(2-(tridecafluorohexyloxy)tetrafluoroethoxy)-2,2-difluoroethanol). The resulting crude product was isolated essentially as described in Example 3 and further purified by recrystallization from cyclohexane/ethyl acetate to yield 1.85 g of purified product.

Example 36

Preparation of 5-Octyl-2-[4-(4-(4-(2-(tridecafluorohexyloxy)tetrafluoroethoxy)-2,2,3,3,4,4-hexafluorobutoxy)butoxy)phenyl]pyrimidine The title compound was prepared essentially as in Example 1 by combining 5-octyl-2-(4-hydrophenyl)pyrimidine (1.02 g, 3.60 mmol) and 4-(2-(tridecafluorohexyloxy)tetrafluoroethoxy)-2,2,3,3,4,4-hexafluorobutoxy)-1-bromobutane (3.03 g, 3.95 mmol; prepared from 1,4-dibromobutane and 4-(2-

(tridecafluorohexyloxy)tetrafluoroethoxy)-2,2,3,3,4,4-hexafluorobutanol). The resulting crude product was isolated and further purified essentially as described in Example 3, eluting with 15 volume percent ethyl acetate/hexane, to yield 2.73 g of purified product.

Example 37

Preparation of 5-Hexyloxy-2-[4-(4-(4-(2-(tridecafluorohexyloxy)tetrafluoroethoxy)-2,2,3,3,4,4-hexafluorobutoxy)butoxy)phenyl]pyrimidine The title compound was prepared essentially as in Example 1 by combining 5-hexyloxy-2-(4-hydrophenyl)pyrimidine (2.0 g, 7.3 mmol) and 4-(2-(tridecafluorohexyloxy)tetrafluoroethoxy)-2,2,3,3,4,4-hexafluorobutoxy)-1-bromobutane (6.1 g, 8.0 mmol, Example 36). The resulting crude product was isolated and further purified by Kugelrohr distillation (b.p. 210°–220° C. at 0.4 torr; yield of 4.5 g). The distilled product was determined to be 96.7% pure by gas chromatographic analysis.

Example 38

Preparation of 5-Octyl-2-[4-(3-(2,2,3,3,4,4,5,5,6,6,6-undecafluorohexyloxy)propoxy)phenyl]pyrimidine The title compound was prepared essentially as in Example 1 by combining 5-octyl-2-(4-hydrophenyl)pyridine (1.0 g, 3.52 mmol) and 3-(2,2,3,3,4,4,5,5,6,6,6-undecafluorohexyloxy)-1-bromopropane (1.69 g, 4.01 mmol; prepared by combining 1,3-dibromopropane with 2,2,3,3,4,4,5,5,6,6,6-undecafluorohexanol). The resulting crude product was isolated and further purified essentially as described in Example 3, eluting with 5 volume percent ethyl acetate/toluene, to yield 1.92 g of purified product.

Example 39

Preparation of 5-Octyl-2-[5-(6-(2,2,3,3,4,4,5,5,6,6,6-undecafluorohexyloxy)hexyloxy)phenyl]pyrimidine The title compound was prepared essentially as in Example 1 by combining 5-octyl-2-(4-hydroxyphenyl)pyrimidine (10.0 g, 35.2 mmol) and 6-(2,2,3,3,4,4,5,5,6,6,6-undecafluorohexyloxy)-1-bromohexane (17.1 g, 36.92 mmol; prepared by combining 1,6-dibromohexane with 2,2,3,3,4,4,5,5,6,6,6-undecafluorohexanol). After refluxing overnight, toluene was added, and the resulting mixture was filtered. The resulting filtrate was concentrated under reduced pressure, was washed with three 30 mL aliquots of perfluorohexane, was diluted with toluene, and was then again concentrated under reduced pressure. The resulting crude product was further purified by recrystallization from ethanol (yield of 17.3 g).

The compounds of Table 1 below were evaluated for transition temperatures by differential scanning calorimetry (DSC) and/or optical observation of material phase changes using a Linkham TMH600 hot stage and a polarizing microscope. The transition temperatures (°C.) were obtained upon cooling through the isotropic state (I) to the smectic A mesophase ($S_A$), the smectic C mesophase ($S_C$), and higher order mesophases (M1 and M2) or the crystalline state (K) and are set forth in the table. Using essentially the method described below for Comparative Example A, cone tilt angle was measured for some of the compounds shown in Table 1.

TABLE 1

Transition Temperatures (°C.) and Cone Tilt Angles (Degrees)

| Example No. | Structure of Compound | I to $S_A$ | to $S_C$ | to $S_{M2}$/K | Tilt Angle |
|---|---|---|---|---|---|
| 1 | $C_8H_{17}$—[pyrimidine]—[phenyl]—$OC_4H_8OCH_2CF_2OC_2F_4OC_4F_9$ | 107 | | 1 | |
| 2 | $C_8H_{17}$—[pyrimidine]—[phenyl]—$OC_5H_{10}OCH_2CF_2OC_2F_4OC_4F_9$ | 104 | (54) | −2 | 18.5 |
| 3 | $C_8H_{17}$—[pyrimidine]—[phenyl]—$OC_3H_6OCH_2CF_2OC_2F_4OC_4F_9$ | 94 | 49 | 15 | 20.5 |
| 4 | $C_8H_{17}$—[pyrimidine]—[phenyl]—$OC_6H_{12}OCH_2CF_2OC_2F_4OC_4F_9$ | 103 | | −3 | |
| 5 | $C_6H_{13}O$—[pyrimidine]—[phenyl]—$OC_5H_{10}OCH_2CF_2OC_2F_4OC_4F_9$ | 127 | 96 | −9 | |

TABLE 1-continued

Transition Temperatures (°C.) and Cone Tilt Angles (Degrees)

| Example No. | Structure of Compound | I to $S_A$ | to $S_C$ | to $S_{M2}$/K | Tilt Angle |
|---|---|---|---|---|---|
| 6 | $C_7H_{15}O$—[pyrimidine]—[phenyl]—$OC_3H_6OCH_2CF_2OC_2F_4OC_4F_9$ | 121 | 92 | <8 | |
| 7 | $C_6H_{13}O$—[pyrimidine]—[phenyl]—$OC_7H_{14}OCH_2CF_2OC_2F_4OC_4F_9$ | 120 | 100 | −14 | |
| 8 | $C_8H_{17}$—[pyrimidine]—[phenyl]—$OC_4H_8OCH_2(CF_2)_4OC_2F_4OC_4F_9$ | 127 | 81 | −3(K) | 17 |
| 9 | $C_8H_{17}$—[pyrimidine]—[phenyl]—$OC_2H_4OCH_2(CF_2)_5OC_2F_4OC_4F_9$ | 127 | 39 | <−5 | |
| 10 | $C_8H_{17}$—[pyrimidine]—[phenyl]—$OC_3H_6OCH_2(CF_2)_5OC_2F_4OC_4F_9$ | 116 | 76 | <−15 | 27 |
| 11 | $C_8H_{17}$—[pyrimidine]—[phenyl]—$OC_4H_8OCH_2(CF_2)_5OC_2F_4OC_4F_9$ | 133 | 89 | 2 | 12.5 |
| 12 | $C_2H_5OC_2H_4O$—[pyrimidine]—[phenyl]—$OC_3H_6OCH_2CF_2OC_2F_4OC_4F_9$ | 115 | 96 | 55 | 35.5 |
| 13 | $C_4H_9O(C_2H_4O)_2$—[pyrimidine]—[phenyl]—$OC_3H_6OCH_2CF_2OC_2F_4OC_4F_9$ | 88 | 39 | 30 | |
| 14 | $C_6H_{13}CHFCH_2O$—[pyrimidine]—[phenyl]—$OC_3H_6OCH_2CF_2OC_2F_4OC_4F_9$ | 121 | 83 | 39 | |
| 15 | $C_6H_{13}O$—[pyrimidine]—[phenyl]—$OC_2H_4OC_2H_4OCH_2CF_2OC_2F_4OC_4F_9$ | 111 | 92 | 11 | |
| 16 | $C_8H_{17}$—[pyrimidine]—[phenyl]—$OC_4H_8OCH_2(CF_2)_3OC_2F_4OC_4F_9$ | 123 | 65 | 2 | |
| 17 | $C_6H_{13}O$—[pyrimidine]—[phenyl]—$OC_3H_6OCH_2CF_2OC_2F_4OC_4F_9$ | 113 | | −8 | |

TABLE 1-continued

Transition Temperatures (°C.) and Cone Tilt Angles (Degrees)

| Example No. | Structure of Compound | I to $S_A$ | to $S_C$ | to $S_{M2}$/K | Tilt Angle |
|---|---|---|---|---|---|
| 18 | 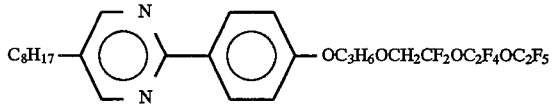 $C_8H_{17}$—pyridine—phenyl—$OC_3H_6OCH_2CF_2OC_2F_4OC_2F_5$ | 84 | | −23 | |
| 19 | 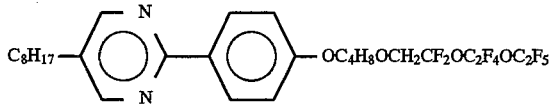 $C_8H_{17}$—pyridine—phenyl—$OC_4H_8OCH_2CF_2OC_2F_4OC_2F_5$ | 104 | | 23 | |
| 20 | 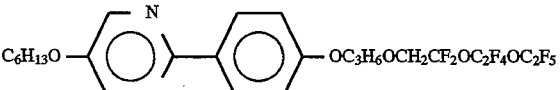 $C_6H_{13}O$—pyridine—phenyl—$OC_3H_6OCH_2CF_2OC_2F_4OC_2F_5$ | 118 | 58 | −6 | |
| 21 | 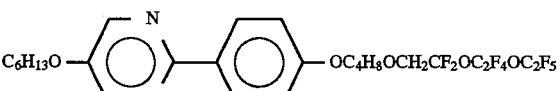 $C_6H_{13}O$—pyridine—phenyl—$OC_4H_8OCH_2CF_2OC_2F_4OC_2F_5$ | 131 | | −9 | |
| 22 | 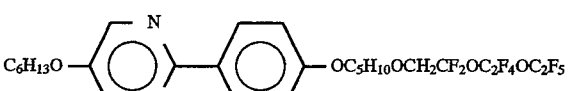 $C_6H_{13}O$—pyridine—phenyl—$OC_5H_{10}OCH_2CF_2OC_2F_4OC_2F_5$ | 128 | 55–60 | <10 | |
| 23 | 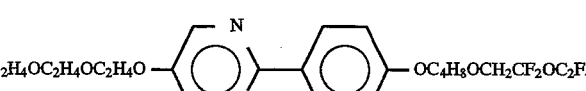 $CH_3OC_2H_4OC_2H_4OC_2H_4O$—pyridine—phenyl—$OC_4H_8OCH_2CF_2OC_2F_4OC_2F_5$ | 100 | 41 mesophase | | |
| 24 | 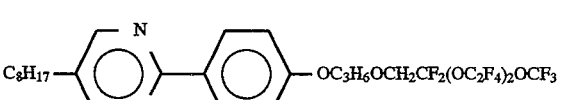 $C_8H_{17}$—pyridine—phenyl—$OC_3H_6OCH_2CF_2(OC_2F_4)_2OCF_3$ | 96 | 26 | −6 | |
| 25 | 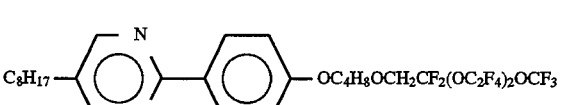 $C_8H_{17}$—pyridine—phenyl—$OC_4H_8OCH_2CF_2(OC_2F_4)_2OCF_3$ | 110 | | 2 | |
| 26 | 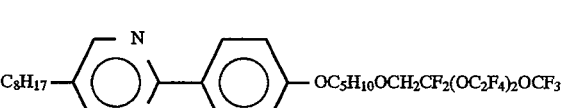 $C_8H_{17}$—pyridine—phenyl—$OC_5H_{10}OCH_2CF_2(OC_2F_4)_2OCF_3$ | 100 | 46 | −9 | |
| 27 | 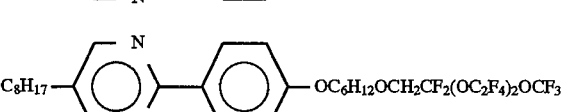 $C_8H_{17}$—pyridine—phenyl—$OC_6H_{12}OCH_2CF_2(OC_2F_4)_2OCF_3$ | 106 | | 12 | |
| 28 | 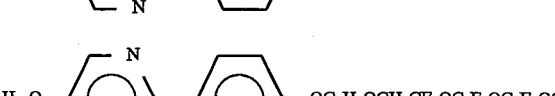 $C_6H_{13}O$—pyridine—phenyl—$OC_3H_6OCH_2CF_2OC_2F_4OC_2F_4OCF_3$ | 128 | 82 | 4 | |
| 29 | 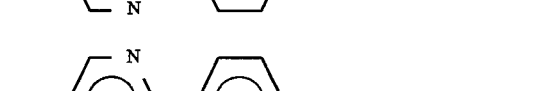 $C_5H_{11}O$—pyridine—phenyl—$OC_3H_6OCH_2CF_2OC_2F_4OC_2F_4OCF_3$ | 125 | 72 | 7 | |

TABLE 1-continued

Transition Temperatures (°C.) and Cone Tilt Angles (Degrees)

| Example No. | Structure of Compound | I to $S_A$ | to $S_C$ | to $S_{M2}$/K | Tilt Angle |
|---|---|---|---|---|---|
| 30 | 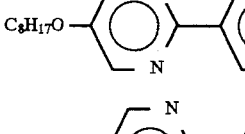 $C_7H_{15}O$—⟨N=N⟩—⟨⟩—$OC_3H_6OCH_2CF_2OC_2F_4OC_2F_4OCF_3$ | 119 | 86 | −8 | |
| 31 | 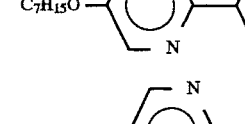 $C_8H_{17}O$—⟨N=N⟩—⟨⟩—$OC_3H_6OCH_2CF_2OC_2F_4OC_2F_4OCF_3$ | 118 | 86 | −17 | |
| 32 | 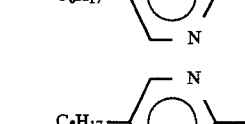 $C_7H_{15}O$—⟨N=N⟩—⟨⟩—$OC_4H_8OCH_2CF_2(OC_2F_4)_2OCF_3$ | 134 | 78 | 5 | |
| 33 | 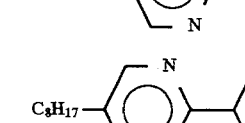 $C_8H_{17}$—⟨N=N⟩—⟨⟩—$OC_5H_{10}OCH_2CF_2OC_4F_9$ | 89 | | −7 | |
| 34 | 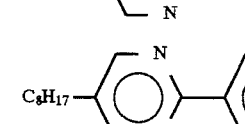 $C_8H_{17}$—⟨N=N⟩—⟨⟩—$OC_6H_{12}OCH_2CF_2OC_4F_9$ | 92 | | 4 | |
| 35 | 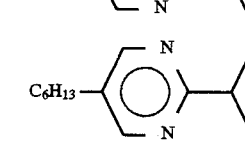 $C_8H_{17}$—⟨N=N⟩—⟨⟩—$OC_4H_8OCH_2CF_2OC_4F_9OC_6F_{13}$ | 109 | | 26 | |
| 36 | 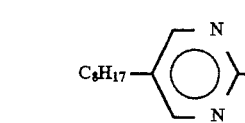 $C_8H_{17}$—⟨N=N⟩—⟨⟩—$OC_4H_8OCH_2(CF_2)_3OC_4F_9OC_6F_{13}$ | 123 | 79 | −5 | |
| 37 | 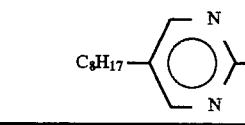 $C_6H_{13}$—⟨N=N⟩—⟨⟩—$OC_4H_8OCH_2C_3F_6OC_2F_4OC_6F_{13}$ | 138 | 113 | −12 | |
| 38 | 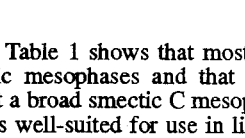 $C_8H_{17}$—⟨N=N⟩—⟨⟩—$OC_3H_6OCH_2C_5F_{11}$ | 80 | | −21 | |
| 39 | 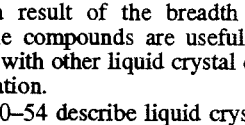 $C_8H_{17}$—⟨N=N⟩—⟨⟩—$OC_6H_{12}OCH_2C_5F_{11}$ | 96 | | 28 | |

The data in Table 1 shows that most of the compounds exhibit smectic mesophases and that many of the compounds exhibit a broad smectic C mesophase, which makes the compounds well-suited for use in liquid crystal display devices. As a result of the breadth of the smectic C mesophase, the compounds are useful in admixture with themselves or with other liquid crystal compounds, even at high concentration.

Examples 40–54 describe liquid crystal compound mixtures and liquid crystal display devices according to the process of the invention.

In each of the following Examples and Comparative Examples, liquid crystal compounds having high cone tilt angles were mixed with various concentrations of liquid crystal compounds having an extended hydrocarbon ether group adjacent to a terminal fluorinated group and having low cone tilt angles (or latent low cone tilt angles), in order to demonstrate the ability of the latter compounds to provide mixtures having a reduced cone tilt angle relative to those of the former compounds. In these Examples, a mixture was prepared and placed into a glass ferroelectric liquid crystal (FLC) test cell having asymmetric alignment layers composed of, e.g., nylon faced with polysiloxane, essentially as described in U.S. Pat. No. 5,377,033 (Radcliffe), the description of which is incorporated herein by reference. The cell was placed on a microscope equipped with a hot stage and a photodetector/oscilloscope. The smectic A to C transition temperature of the mixture was determined by heating the test cell to the smectic A phase of the mixture without an applied electric field (electrodes shorted), aligning the cell to obtain extinction between crossed polarizers, then slowly cooling and watching for a waveform shift on the oscilloscope. The reduced temperature for each subsequent data point was calculated by subtracting the smectic A to C transition temperature from the hot stage temperature. Then a square wave signal was applied to the cell at a field of 12.5 V/micron, and cone tilt angle data was collected at each reduced temperature by measuring and averaging the angle between "off" states (smectic C extinction) on either side of the smectic A extinction angle. Cone tilt angle data was collected for each mixture at reduced temperatures of −1° C., −5° C., −10° C., −15° C., −20° C., −30° C., −40° C., and −50° C. and is shown in Table 2 below. The mesophases of the mixtures were also determined (essentially as described above for individual compounds) and are shown in Table 3.

Comparative Example A 95 weight percent 5-octyloxy-2-[4-(2-(2-(nonafluorobutoxy)tetrafluoroethoxy)-2,2-difluoroethoxy)phenyl]pyrimidine (prepared essentially as in Example 80 of U.S. Pat. No. 5,437,812 (Janulis)) and 5 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine as a high polarization additive (which can be prepared essentially as described below) were combined in a small vial at room temperature, and the resulting combination was heated to the isotropic state with manual roller mixing.

Preparation of 5-Octyl-2-[4-((R)-2-fluoro-3-(2-(2-(nonafluorobutoxy)tetrafluoroethoxy)-2,2,-difluoroethoxy)propoxy)phenyl]pyrimidine A solution of 5-octyl-2-[4-((S)-2-hydroxy-3-(2-(2-(nonafluorobutoxy) tetrafluoroethoxy)-2,2,-difluoroethoxy) propoxy)phenyl]pyrimidine (prepared essentially as described below, 8.0 g, 10.35 mmol) in dry tetrahydrofuran (50 ml) was added dropwise to a −70° C. solution of diethylaminosulfur trifluoride (3.3 g, 20.7 mmol) in tetrahydrofuran (50 ml). The resulting mixture was warmed to −30° C. over a period of 2 hours, and then pyridine (3.3 g, 41.4 mmol) was added to the mixture. The mixture was allowed to warm to ambient temperature and was stirred for 12 hours. The mixture was then poured into a slurry of silica gel (40 g) in diethyl ether and was concentrated onto the silica gel under reduced pressure. The product-coated silica was placed on top of 100 g of fresh silica gel and was eluted with a 10:1 hexanes/ethyl acetate solution. Fractions collected containing the product were concentrated under reduced pressure. The product was then recrystallized from methanol to give 4.9 g of the title compound as a white solid.

Preparation of 5-Octyl-2-[4-((S)-2-hydroxy-3-(2-(2-(nonafluorobutoxy)tetrafluoroethoxy)-2,2,-difluoroethoxy)propoxy)phenyl]pyrimidine A solution of potassium hydroxide (1.97 g, 35 mmol) in water (1.97 ml) was added to a solution of (S)-5-octyl-2-[4-(2,3-oxiranylpropoxy)phenyl]pyrimidine (10.0 g, 29.3 mmol) (prepared essentially as described by Sakaguchi et al. in Ferroelectrics 114, 269 (1992)), 2,2-difluoro-2-[1,1,2,2-tetrafluoro-2-nonfluorobutoxy) ethanol](15.2 g, 35.16 mmol), and tetrabutyl ammonium hydrogen sulfate (500 mg, 1.5 mmol) in tetrahydrofuran (20 ml). The resulting mixture was heated to reflux temperature for 23 hours, was diluted with water (100 ml), and was extracted with three 100 ml aliquots of ethyl acetate. The organic extracts were concentrated under reduced pressure, and the resulting product was recrystallized from acetonitrile (150 ml) to give -2-[4-((S)-2-hydroxy-3-(2-(2-(nonafluorobutoxy)1,1,2,2-tetrafluoroethoxy)-2,2,-difluoroethoxy)propoxy)phenyl]-5-octyl-pyrimidine as a white solid.

Example 40

31.5 weight percent 5-octyl-2-[4-(6-(2-(nonafluorobutoxy)-2,2-difluoroethoxy)hexyloxy)phenyl] pyrimidine (Example 34), 63.6 weight percent 5-octyloxy-2-[4-(2-(2-(nonafluorobutoxy) tetrafluoroethoxy)-2,2-difluoroethoxy)phenyl]pyrimidine, and 4.9 weight percent 5-octyl-2-[4-((R)-2-fluoro-3-(2-(2-(nonfluorobutoxy)tetrafluoroethoxy)-2,2-difluoroethoxy)propoxy)phenyl] pyrimidine (as a high polarization additive) were combined essentially as described in Comparative Example A.

Example 41

47.5 weight percent 5-octyl-2-[4-(6-(2-(nonafluorobutoxy)-2,2-difluoroethoxy)hexyloxy)phenyl] pyrimidine (Example 34 ), 47.8 weight percent 5-octyloxy-2-[4-(2-(2-(nonafluorobutoxy)tetrafluoroethoxy)-2,2-difluoroethoxy) phenyl]pyrimidine, and 5.2 weight percent 5-octyl-2-[4-((R)-2-fluoro-3-(2-(2-(nonfluorobutoxy)tetrafluoroethoxy)-2,2-difluoroethoxy) propoxy) phenyl] pyrimidine (as a high polarization additive) were combined essentially as described in Comparative Example A.

Example 42

31.8 weight percent 5-hexyloxy-2-[4-(4-(2-(2-(pentafluoroethoxy)tetrafluoroethoxy)2,2-difluoroethoxy)butoxy) phenyl]pyrimidine (Example 21), 63.2 weight percent 5-octyloxy-2-[4-(2-(2-(nonafluorobutoxy)tetrafluoroethoxy)-2,2-difluoroethoxy)phenyl]pyrimidine, and 4.9 weight percent 5-octyl-2-[4-((R)-2-fluoro-3-(2-(2-(nonfluorobutoxy) tetrafluoroethoxy)-2,2-difluoroethoxy) propoxy)phenyl]pyrimidine (as a high polarization additive) were combined essentially as described in Comparative Example A.

Example 43

47.4 weight percent 5-hexyloxy-2-[4-(4-(2-(2-(pentafluoroethoxy)tetrafluoroethoxy)2,2-difluoroethoxy)butoxy)phenyl]pyrimidine (Example 21), 47.7 weight percent 5-octyloxy-2-[4-(2-(2-(nonafluorobutoxy)tetrafluoroethoxy)-2,2-difluoroethoxy)phenyl]pyrimidine, and 5.0 weight percent 5-octyl-2-[4-((R)-2-fluoro-3-(2-(2-(nonfluorobutoxy) tetrafluoroethoxy)-2,2-difluoroethoxy) propoxy)phenyl]pyrimidine (as a high polarization additive) were combined essentially as described in Comparative Example A.

Example 44

31.7 weight percent 5-octyl-2-[4-(6-(2-(2-(nonafluorobutoxy)tetrafluoroethoxy)-2,2-difluoroethoxy) hexyloxy)phenyl]pyrimidine (Example 4), 63.4 weight percent 5-octyloxy-2-[4-(2-(2-(nonafluorobutoxy) tetrafluoroethoxy)-2,2-difluoroethoxy)phenyl]pyrimidine, and 4.9 weight percent 5-octyl-2-[4-((R)-2-fluoro-3-(2-(2-(nonfluorobutoxy)tetrafluoroethoxy)-2,2-difluoroethoxy) propoxy)phenyl]pyrimidine (as a high polarization additive) were combined essentially as described in Comparative Example A.

Example 45

47.4 weight percent 5-octyl-2-[4-(6-(2-(2-(nonafluorobutoxy)tetrafluoroethoxy)-2,2-difluoroethoxy) hexyloxy)phenyl]pyrimidine (Example 4), 47.4 weight percent 5-octyloxy-2-[4-(2-(2-(nonafluorobutoxy) tetrafluoroethoxy)-2,2-difluoroethoxy)phenyl]pyrimidine, and 5.2 weight percent 5-octyl-2-[4-((R)-2-fluoro-3-(2-(2-(nonfluorobutoxy)tetrafluoroethoxy)-2,2-difluoroethoxy) propoxy)phenyl]pyrimidine (as a high polarization additive) were combined essentially as described in Comparative Example A.

Example 46

47.4 weight percent 5-octyl-2-[4-(4-(4-(2-(tridecafluorohexyloxy)tetrafluoroethoxy)-2,2,3,3,4,4-hexafluorobutoxy)butoxy)phenyl]pyrimidine (Example 36) 47.5 weight percent 5-octyloxy-2-[4-(2-(2-(nonafluorobutoxy)tetrafluoroethoxy)-2,2-difluoroethoxy) phenyl]pyrimidine, and 5.2 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Comparative Example B 95 weight percent 5-octyl-2-[4-(6-(2-(2-(2-(trifluoromethoxy)tetrafluoroethoxy)tetrafluoroethoxy) tetrafluoroethoxy)-2,2,3,3,4,4,5,5,6,6-decafluorohexyloxy) phenyl]pyrimidine (prepared essentially as in Example 110 of U.S. Ser. No. 08/338957) and 5 weight percent 5-octyl-2-[4-((R)-2-fluoro-3-(2-(2-(nonfluorobutoxy) tetrafluoroethoxy)-2,2-difluoroethoxy)propoxy)phenyl] pyrimidine (as a high polarization additive) were combined essentially as described in Comparative Example A.

Example 47

47.4 weight percent 5-octyl-2-[4-(4-(4-(2-(tridecafluorohexyloxy)tetrafluoroethoxy)-2,2,3,3,4,4-hexafluorobutoxy)butoxy)phenyl]pyrimidine (Example 36), 47.5 weight percent 5-octyl-2-[4-(6-(2-(2-(2-(trifluoromethoxy)tetrafluoroethoxy)tetrafluoroethoxy) tetrafluoroethoxy)-2,2,3,3,4,4,5,5,6,6-decafluorohexyloxy) phenyl]pyrimidine, and 5.2 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Comparative Example C 47.4 weight percent 5-octyl-2-[4-(6-(2-(nonafluorobutoxy)-2,2-difluoroethoxy)hexyloxy)phenyl] pyrimidine (Example 34), 47.4 weight percent 5-octyl-2-[4-(6-(2-(2-(2-(trifluoromethoxy)tetrafluoroethoxy) tetrafluoroethoxy)tetrafluoroethoxy)-2,2,3,3,4,4,5,5,6,6-decafluorohexyloxy)phenyl]pyrimidine, and 5.1 weight percent 5-octyl-2-[4-((R)-2-fluoro-3-(2-(2-(nonfluorobutoxy)tetrafluoroethoxy)-2,2-difluoroethoxy) propoxy)phenyl]pyrimidine (as a high polarization additive) were combined essentially as described in Comparative Example A.

Due to concentration effects, the resulting combination yielded no smectic A to smectic C transition temperature, and the tilt angle of the mixture could not be measured.

Comparative Example D 47.5 weight percent 5-octyl-2-[4-(6-(2-(2-(nonafluorobutoxy)tetrafluoroethoxy)-2,2-difluoroethoxy) hexyloxy)phenyl]pyrimidine (Example 4), 47.5 weight percent 5-octyl-2-[4-(6-(2-(2-(2-(trifluoromethoxy) tetrafluoroethoxy)tetrafluoroethoxy)tetrafluoroethoxy)-2,2, 3,3,4,4,5,5,6,6-decafluorohexyloxy)phenyl]pyrimidine, and 4.9 weight percent 5-octyl-2-[4-((R)-2-fluoro-3-(2-(2-(nonfluorobutoxy)tetrafluoroethoxy)-2,2-difluoroethoxy) propoxy)phenyl]pyrimidine (as a high polarization additive) were combined essentially as described in Comparative Example A.

Due to concentration effects, the resulting combination yielded no smectic A to smectic C transition temperature, and the tilt angle of the mixture could not be measured.

Comparative Example E 95 weight percent 5-octyl-2-[4-(10-(2-(nonafluorobutoxy)tetrafluoroethoxy)-2,2,3,3,4,4,5,5,6,6,7, 7,8,8,9,9,10,10-octadecafluorodecyloxy)phenyl]pyrimidine (prepared essentially as in Example 111 of U.S. Ser. No. 08/338957) and 5 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Example 48

47.6 weight percent 5-octyl-2-[4-(4-(4-(2-(tridecafluorohexyloxy)tetrafluoroethoxy)-2,2,3,3,4,4-hexafluorobutoxy)butoxy)phenyl]pyrimidine (Example 36), 47.4 weight percent 5-octyl-2-[4-(10-(2-(nonafluorobutoxy) tetrafluoroethoxy)-2,2,3,3,4,4,5,5,6,6,7,7,8,8,9,9,10,10-octadecafluorodecyloxy)phenyl]pyrimidine (prepared essentially as in Example 101 of U.S. Ser. No. 08/338957), and 5.0 weight percent 5-octyl-2-[4-((R)-2-fluoro-3-(2-(2-(nonfluorobutoxy)tetrafluoroethoxy)-2,2-difluoroethoxy) propoxy)phenyl]pyrimidine (as a high polarization additive) were combined essentially as described in Comparative Example A.

Example 49

47.5 weight percent 5-octyl-2-[4-(6-(2-(nonafluorobutoxy)-2,2-difluoroethoxy)hexyloxy)phenyl] pyrimidine (Example 34), 47.3 weight percent 5-octyl-2-[4-(10-(2-(nonafluorobutoxy)tetrafluoroethoxy)-2,2,3,3,4,4,5, 5,6,6,7,7,8,8,9,9,10,10-octadecafluorodecyloxy)phenyl] pyrimidine, and 5.2 weight percent 5-octyl-2-[4-((R)-2-fluoro-3-(2-(2-(nonfluorobutoxy)tetrafluoroethoxy)-2,2-difluoroethoxy) propoxy) phenyl]pyrimidine (as a high polarization additive) were combined essentially as described in Comparative Example A.

Example 50

47.5 weight percent 5-octyl-2-[4-(6-(2-(2-(nonafluorobutoxy)tetrafluoroethoxy)-2,2-difluoroethoxy) hexyloxy)phenyl]pyrimidine (Example 4), 47.7 weight percent 5-octyl-2-[4-(10-(2-(nonafluorobutoxy) tetrafluoroethoxy)-2,2,3,3,4,4,5,5,6,6,7,7,8,8,9,9,10,10-octadecafluorodecyloxy)phenyl]pyrimidine, and 4.8 weight percent 5-octyl-2-[4-((R)-2-fluoro-3-(2-(2-(nonfluorobutoxy) tetrafluoroethoxy)-2,2-difluoroethoxy) propoxy)phenyl]pyrimidine (as a high polarization additive) were combined essentially as described in Comparative Example A.

Comparative Example F 95 weight percent 5-octyl-2-[4-(4-(2-(tridecafluorohexyloxy)tetrafluoroethoxy)-2,2,3,3,4,4- hexafluorobutoxy)phenyl]pyrimidine (prepared essentially as in Example 116 of U.S. Ser. No. 08/338957) and 5 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Example 51

47.5 weight percent 5-octyl-2-[4-(4-(4-(2-(tridecafluorohexyloxy)tetrafluoroethoxy)-2,2,3,3,4,4-hexafluorobutoxy)butoxy)phenyl]pyrimidine (Example 36), 47.3 weight percent 5-octyl-2-[4-(4-(2-(tridecafluorohexyloxy)tetrafluoroethoxy)-2,2,3,3,4,4-hexafluorobutoxy)phenyl]pyrimidine, and 5.1 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Comparative Example G 47.3 weight percent 5-octyl-2-[4-(6-(2-(2-(nonafluorobutoxy)tetrafluoroethoxy)-2,2-difluoroethoxy)hexyloxy)phenyl]pyrimidine (Example 4), 47.5 weight percent 5-octyl-2-[4-(4-(2-(tridecafluorohexyloxy)tetrafluoroethoxy)-2,2,3,3,4,4-hexafluorobutoxy)phenyl]pyrimidine, and 5.2 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Due to concentration effects, the resulting combination yielded no smectic A to smectic C transition temperature, and the tilt angle of the mixture could not be measured.

Comparative Example H 95 weight percent 5-octyl-2-[4-(6-(2-(nonafluorobutoxy)tetrafluoroethoxy)-2,2,3,3,4,4,5,5,6,6-decafluorohexyloxy)phenyl]pyrimidine (prepared essentially as in Example 99 of U.S. Ser. No. 08/338957) and 5 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Example 52

47.4 weight percent 5-octyl-2-[4-(4-(4-(2-(tridecafluorohexyloxy)tetrafluoroethoxy)-2,2,3,3,4,4-hexafluorobutoxy)butoxy)phenyl]pyrimidine (Example 36), 47.5 weight percent 5-octyl-2-[4-(6-(2-(nonafluorobutoxy)tetrafluoroethoxy)-2,2,3,3,4,4,5,5,6,6-decafluorohexyloxy)phenyl]pyrimidine (prepared essentially as in Example 107 of U.S. Ser. No. 08/338957), and 5.2 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Comparative Example I 47.5 weight percent 5-octyl-2-[4-(6-(2-(nonafluorobutoxy)-2,2-difluoroethoxy)hexyloxy)phenyl]pyrimidine (Example 34), 47.4 weight percent 5-octyl-2-[4-(6-(2-(nonafluorobutoxy)tetrafluoroethoxy)-2,2,3,3,4,4,5,5,6,6-decafluorohexyloxy)phenyl]pyrimidine, and 5.0 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Due to concentration effects, the resulting combination yielded no smectic A to smectic C transition temperature, and the tilt angle of the mixture could not be measured.

Comparative Example J 47.4 weight percent 5-octyl-2-[4-(6-(2-(2-(nonafluorobutoxy)tetrafluoroethoxy)-2,2-difluoroethoxy)hexyloxy)phenyl]pyrimidine (Example 4), 47.3 weight percent 5-octyl-2-[4-(6-(2-(nonafluorobutoxy)tetrafluoroethoxy)-2,2,3,3,4,4,5,5,6,6-decafluorohexyloxy)phenyl]pyrimidine, and 5.4 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Due to concentration effects, the resulting combination yielded no smectic A to smectic C transition temperature, and the tilt angle of the mixture could not be measured.

Comparative Example K 95 weight percent 5-octyl-2-[4-(6-(2-(2-(nonafluorobutoxy)tetrafluoroethoxy)tetrafluoroethoxy-2,2,3,3,4,4,5,5,6,6-decafluorohexyloxy)phenyl]pyrimidine (prepared essentially as in Example 104 of U.S. Ser. No. 08/338957) and 5 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Example 53

47.4 weight percent 5-octyl-2-[4-(4-(4-(2-(tridecafluorohexyloxy)tetrafluoroethoxy)-2,2,3,3,4,4-hexafluorobutoxy)butoxy)phenyl]pyrimidine (Example 36), 47.5 weight percent 5-octyl-2-[4-(6-(2-(2-(nonafluorobutoxy)tetrafluoroethoxy)tetrafluoroethoxy-2,2,3,3,4,4,5,5,6,6-decafluorohexyloxy)phenyl]pyrimidine (prepared essentially as in Example 104 of U.S. Ser. No. 08/338957), and 5.2 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Comparative Example L 47.7 weight percent 5-octyl-2-[4-(6-(2-(nonafluorobutoxy)-2,2-difluoroethoxy)hexyloxy)phenyl]pyrimidine (Example 34), 47.3 weight percent 5-octyl-2-[4-(6-(2-(2-(nonafluorobutoxy)tetrafluoroethoxy)tetrafluoroethoxy-2,2,3,3,4,4,5,5,6,6-decafluorohexyloxy)phenyl]pyrimidine, and 5.2 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Due to concentration effects, the resulting combination yielded no smectic A to smectic C transition temperature, and the tilt angle of the mixture could not be measured.

Comparative Example M 47.7 weight percent 5-octyl-2-[4-(6-(2-(2-(nonafluorobutoxy)tetrafluoroethoxy)-2,2-difluoroethoxy)

hexyloxy)phenyl]pyrimidine (Example 4), 47.4 weight percent 5-octyl-2-[4-(6-(2-(2-(nonafluorobutoxy)tetrafluoroethoxy)tetrafluoroethoxy-2,2,3,3,4,4,5,5,6,6-decafluorohexyloxy)phenyl]pyrimidine, and 4.9 weight percent 5-octyl-2-[4-((R)-2-fluoro-3-(2-(2-(nonfluorobutoxy)tetrafluoroethoxy)-2,2-difluoroethoxy)propoxy) phenyl]pyrimidine (as a high polarization additive) were combined essentially as described in Comparative Example A.

Due to concentration effects, the resulting combination yielded no smectic A to smectic C transition temperature, and the tilt angle of the mixture could not be measured.

Comparative Example N 47.5 weight percent 5-octyl-2-[4-(4-(2-(nonafluorobutoxy)tetrafluoroethoxy)-4,4-difluorobutoxy)phenyl]pyrimidine (prepared essentially as in Example 114 of U.S. Ser. No. 08/338957 using 4,4-difluoro-4 (perfluorobutoxyethoxy)-butanol), 47.7 weight percent 5-octyloxy-2-[4-(2-(2-(nonafluorobutoxy)tetrafluoroethoxy)-2,2-difluoroethoxy)phenyl]pyrimidine, and 5.2 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Comparative Example O 47.5 weight percent 5-octyl-2-[4-(5-(2-(nonafluorobutoxy) tetrafluoroethoxy)-5,5-difluoropentoxy)phenyl]pyrimidine (prepared essentially as in Example 114 of U.S. Ser. No. 08/338957), 47.7 weight percent 5-octyloxy-2-[4-(2-(2-(nonafluorobutoxy)tetrafluoroethoxy)-2,2-difluoroethoxy)phenyl]pyrimidine, and 5.2 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Comparative Example P 47.5 weight percent 5-octyl-2-[4-(10-(2-(nonafluorobutoxy)tetrafluoroethoxy)-4,4,5,5,6,6,7,7,8,8-decafluorooctyloxy)phenyl]pyrimidine (prepared essentially as in Example 115 of U.S. Ser. No. 08/338957), 47.7 weight percent 5-octyloxy-2-[4-(2-(2-(nonafluorobutoxy)tetrafluoroethoxy)-2,2-difluoroethoxy)phenyl]pyrimidine, and 5.2 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (as a high polarization additive) were combined essentially as described in Comparative Example A.

Example 54

47.6 weight percent 5-octyl-2-(4-(2-(2-(2,2,3,3,4,4,5,5,6,6,7,7,8,8,8-pentadecafluorooctyloxy)ethoxy)ethoxy)phenyl)pyrimidine (prepared essentially as in Example 75 of U.S. Pat. No. 5,437,812), 47.6 weight percent 5-octyloxy-2-[4-(2-(2-(nonafluorobutoxy)tetrafluoroethoxy)-2,2-difluoroethoxy)phenyl]pyrimidine, and 4.9 weight percent 5-octyl-2-[4-((R)-2-fluoro-3-(2-(2-(nonfluorobutoxy)tetrafluoroethoxy)-2,2-difluoroethoxy)propoxy)phenyl] pyrimidine (as a high polarization additive) were combined essentially as described in Comparative Example A.

TABLE 2

| | Cone Tilt Angles (Degrees) | | | | | | | |
|---|---|---|---|---|---|---|---|---|
| Example | Reduced Temperature (°C.) | | | | | | | |
| No. | −1 | −5 | −10 | −15 | −20 | −30 | −40 | −50 |
| Comp. A | 10 | 26.5 | 31.2 | | 32.5 | 34.5 | 33.5 | |
| 40 | 16.0 | 21.5 | 25.5 | 26.0 | 27.5 | 27.5 | 27.5 | 27.5 |
| 41 | 10.5 | 15.5 | 18.0 | 19.5 | 20.5 | 20.5 | 20.5 | |
| 42 | 15.5 | 22.5 | 25.5 | 26.0 | 26.5 | 26.5 | 28.5 | 28.5 |
| 43 | 13.0 | 16.0 | 18.0 | 19.5 | 21.5 | 21.5 | 21.5 | 21.5 |
| 44 | 18.0 | 24.5 | 26.5 | 27.5 | 27.5 | 27.5 | 29.5 | 29.5 |
| 45 | 13.0 | 17.5 | 19.5 | 22.0 | 22.5 | 24.0 | 24.0 | 24.0 |
| 46 | 18.5 | 23.0 | 23.25 | 23.5 | 25.0 | 25.25 | 26.0 | 25.5 |
| Comp. B | 21.5 | 25.25 | 23.25 | 27.5 | 27.65 | 29.0 | 30.5 | |
| 47 | 9.5 | 15.5 | 18.0 | 20.0 | 21.0 | 21.5 | 21.5 | |
| Comp. E | 12.6 | 20.9 | 27.9 | 30.75 | 31.25 | | | |
| 48 | 11.0 | 19.0 | 24.0 | 26.5 | 28.0 | 30.0 | 31.5 | 31.5 |
| 49 | 12.5 | 15.0 | 17.0 | 17.5 | 17.5 | 18.0 | 18.0 | |
| 50 | 17.0 | 22.0 | 24.5 | 25.0 | 26.5 | 26.5 | 26.5 | 26.5 |
| Comp. F | 18.0 | 25.0 | 26.0 | 28.5 | 29.5 | 29.5 | 29.5 | 29.5 |
| 51 | 14.5 | 16.0 | 18.5 | 18.5 | 18.5 | 18.5 | | |
| Comp. H | 18.5 | 23.25 | 25.75 | 26.75 | 27.5 | 28.25 | 29.0 | |
| 52 | 11.0 | 16.5 | 16.5 | 18.5 | 18.5 | 18.5 | 18.5 | |
| 53 | 18.5 | 21.5 | 15.3 | 25.0 | 25.0 | 26.0 | 26.0 | |
| 54 | 14.0 | 20.0 | 23.25 | 24.0 | 25.0 | 25.5 | | |
| Comp. K | | | 29.0 | 30.5 | 31.8 | | | |
| Comp. N | 22.0 | 26.0 | 27.5 | 31.5 | 32.5 | 31.0 | 32.5 | 32.5 |
| Comp. O | 15.0 | 20.5 | 23.5 | 24.5 | 25.5 | 25.5 | 27.5 | 27.5 |
| Comp. P | 12.5 | 25.5 | 29.5 | 32.5 | 33.0 | 33.5 | 33.5 | 33.5 |

TABLE 3

| | Transition Temperatures (°C.) | | |
|---|---|---|---|
| Example No. | I to A | A to C | C to K |
| Comp. A | 95 | 83 | 47 |
| 40 | 101.8 | 74.4 | 8.6 |
| 41 | 103.0 | 62.6 | <−10 |
| 42 | 120.9 | 85.2 | −2.7 |
| 43 | 126.5 | 78.5 | <−10 |
| 44 | 104.4 | 75.4 | 6.8 |
| 45 | 106.9 | 66.9 | <−15 |
| 46 | 109.9 | 69.0 | −8.7 |
| Comp. B | 113.3 | 64.8 | −31 |
| 47 | 118.6 | 58.0 | <−10 |
| Comp. C | 109.8 | none | <−10 |
| Comp. D | 114.8 | none | <−10 |
| Comp. E | 121.6 | 85.2 | 26.8 |
| 48 | 124.1 | 82.7 | <−10 |
| 49 | 115.7 | 58.8 | <−10 |
| 50 | 120.1 | 76.8 | <−10 |
| Comp. F | 95.1 | 52.7 | 2.9 |
| 51 | 109.4 | 48.4 | <−10 |
| Comp. G | 108.8 | none | <−10 |
| Comp. H | 115.6 | 65.4 | <−10 |
| 52 | 118.8 | 56.7 | <−10 |
| Comp. I | 108.8 | none | <−10 |
| Comp. J | 112.2 | none | <−10 |
| Comp. K | 112 | 63 | −14 |
| 53 | 118.0 | 62.0 | <−10 |
| Comp. L | 110.4 | none | <−10 |
| Comp. M | 112.3 | none | <−10 |
| Comp. N | 96.9 | 76.2 | 13.6 |
| Comp. O | 104.3 | 67.9 | −3.5 |
| Comp. P | 118.8 | 82.7 | 9.4 |
| 54 | 96.5 | 65.7 | 11.5 |

The data in Table 2 shows that the liquid crystal compound mixtures of the Comparative Examples (hereinafter, the comparative mixtures) had cone tilt angles generally in excess of the ideal 22.5 degrees. When liquid crystal compounds of Formula I, supra, were added to the comparative mixtures, the cone tilt angles of the mixtures were reduced, as shown by the following comparisons:

Comparative Example A/Examples 40–46 and 54
Comparative Example B/Example 47
Comparative Example E/Examples 48–50
Comparative Example F/Example 51
Comparative Example H/Example 52

Comparative Examples N, O, and P showed the effect of the addition (to base mixtures) of liquid crystal compounds which did not possess an extended hydrocarbon ether group adjacent to a terminal fluorinated group. Such compounds were not as effective in reducing tilt angle while substantially maintaining the tilted smectic mesophase of the base mixture as were compounds which did possess such an extended group (see, e.g., Examples 41, 45, and 46).

The data in Table 3 shows that the above-described liquid crystal compounds (which do possess an extended hydrocarbon ether group adjacent to a terminal fluorinated group), when used in base mixtures according to the process of the invention, advantageously produce a relatively low suppression (and, in some cases, even a broadening) of the smectic C mesophase of the base mixtures.

Various modifications and alterations of this invention will become apparent to those skilled in the art without departing from the scope and spirit of this invention.

We claim:

1. A process for controlling the cone tilt angle of a tilted smectic liquid crystal composition comprising the step of combining (a) at least one liquid crystal composition comprising at least one smectic or latent smectic liquid crystal compound comprising (i) an aliphatic fluorocarbon terminal portion comprising a terminal fluoroalkyl or fluoroether group and an alkylene group having at least two carbon atoms and containing at least one catenary ether oxygen atom, (ii) an aliphatic hydrocarbon terminal portion, and (iii) a central core connecting said terminal portions; and (b) at least one liquid crystal composition comprising at least one smectic or latent smectic liquid crystal compound; with the provisos that at least one of said compositions (a) and (b) comprises at least one chiral liquid crystal compound and that said combining of compositions (a) and (b) provides an optically active, tilted chiral smectic liquid crystal composition.

2. The process of claim 1 wherein said composition (a) is utilized in an amount such that the resulting combination has a cone tilt angle between about 10 and about 35 degrees.

3. The process of claim 1 wherein said aliphatic fluorocarbon terminal portion is represented by the formula —D—$R_h$—$R_f$, where $R_h$ is an alkylene group having at least two carbon atoms and containing at least one catenary ether oxygen atom; $R_f$ is fluoroalkyl or fluoroether; and D is non-directionally selected from the group consisting of a covalent bond, —C(=O)O—$C_rH_{2r}$—, —O—$C_rH_{2r}$—, —O—($C_sH_{2s}$O)$_t$—$C_r$—$H_{2r}$—, —$C_rH_{2r}$—, —($C_sH_{2s}$O)$_t$—$C_r$—$H_{2r}$—, —OSO$_2$—, —SO$_2$—, —SO$_2$—$C_rH_{2r}$—,

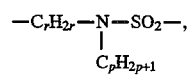

—C≡C—, —CH=CH—, —C(=O)—, —O(O=)C—$C_rH_{2r}$—,

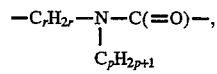

—CH=N—, —O—, —S—, —N($C_pH_{2p+1}$)—, and combinations thereof, where r and r' are independently integers of 0 to 20, s is independently an integer of 1 to 10 for each ($C_sH_{2s}$O), t is an integer of 1 to 6, and p is an integer of 0 to 4.

4. The process of claim 3 wherein said $R_f$ is perfluoroalkyl or perfluoroether and contains from 1 to 20 carbon atoms; said $R_h$ contains from 2 to 12 carbon atoms; and said D is selected from the group consisting of —O—, —C(=O)—, a covalent bond, and combinations thereof.

5. The process of claim 4 wherein said $R_h$ contains from 2 to 8 carbon atoms and said D is —O—.

6. The process of claim 1 wherein said smectic or latent smectic liquid crystal compound of said composition (a) is represented by the general formula I:

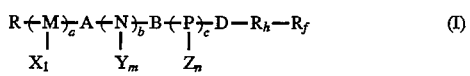

where M, N, and P are each independently selected from the group consisting of

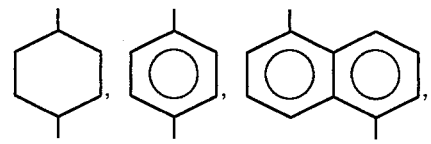

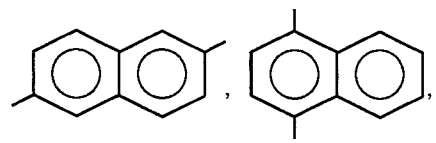

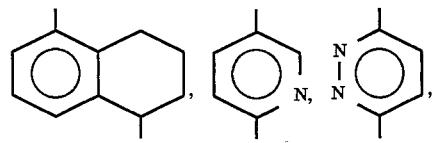

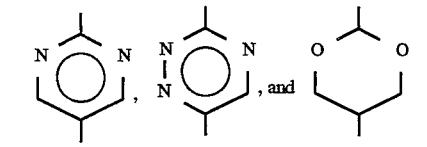

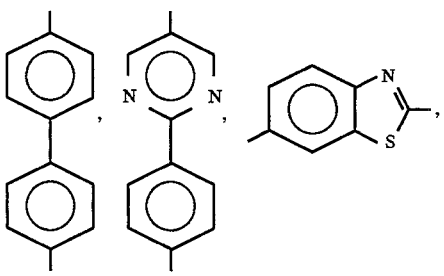

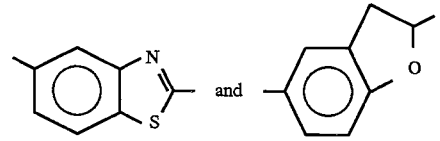

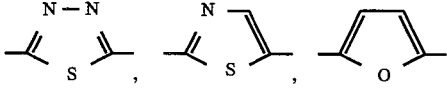

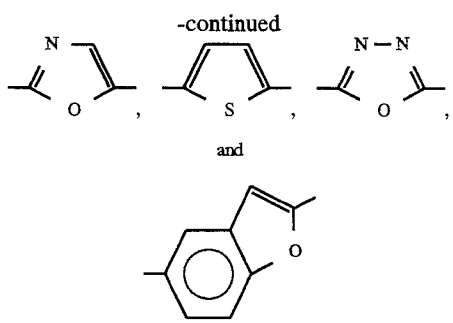

and a, b, and c are each independently zero or an integer of from 1 to 3, with the proviso that the sum of a+b+c be at least 1;

each A and B are non-directionally and independently selected from the group consisting of a covalent bond, —C(=O)—O—, —C(=O)—S—, —C(=O)—Se—, —C(=O)—Te—, —(CH$_2$CH$_2$)$_k$— where k is 1 to 4, —CH=CH—, —C≡C—, —CH=N—, —CH$_2$—O—, —C(=O)—, and —O—;

each X, Y, and Z are independently selected from the group consisting of —H, —Cl, —F, —Br, —I, —OH, —OCH$_3$, —CH$_3$, —CF$_3$, —OCF$_3$, —CN, and —NO$_2$;

each l, m, and n are independently zero or an integer of 1 to 4;

D is non-directionally selected from the group consisting of a covalent bond, —C(=O)—O—C$_r$H$_{2r}$—, —O—C$_r$H$_{2r}$—, —O—(O=)C—C$_r$H$_{2r}$—, —C≡C—, —CH=CH—, —C(=O)—, —O—(C$_s$H$_{2s}$O)$_t$C$_r$H$_{2r}$—, —C$_r$H$_{2r}$—, —(C$_s$H$_{2s}$O)$_t$C$_r$ H$_{2r}$—, —O—, —S—, —OSO$_2$—, —SO$_2$—, —SO$_2$—C$_r$H$_{2r}$—,

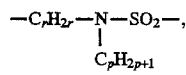

—N(C$_p$H$_{2p+1}$)—,

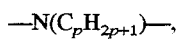

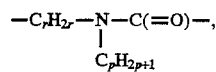

—CH=N—, and combinations thereof, where r and r' are independently integers of 0 to 20, s is independently an integer of 1 to 10 for each (C$_s$H$_{2s}$O), t is an integer of 1 to 6, and p is an integer of 0 to 4;

R is selected from the group consisting of —O—(C$_{q'}$H$_{2q'-v'}$—(R')$_{v'}$—O)$_w$—C$_q$H$_{2q+1-v}$—(R')$_v$, —((C$_{q'}$H$_{2q'-v'}$—(R')$_{v'}$—O)$_w$—C$_q$H$_{2q+1-v}$—(R')$_v$, —C(=O)—O—C$_q$H$_{2q+1-v}$—(R')$_v$, —O—(O=)C—C$_q$H$_{2q+1-v}$—(R')$_v$,

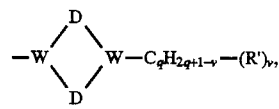

—CR'H—(D)$_g$—CR'H—C$_q$H$_{2q+1-v}$—(R')$_v$, where each R' is independently selected from the group consisting of —Cl, —F, —CF$_3$, —NO$_2$, —CN, —H, —C$_q$H$_{2q+1}$, —O—(O=)C—C$_q$H$_{2q+1}$, —C(=O)—O—C$_q$H$_{2q+1}$, —Br, —OH, and —OC$_q$H$_{2q+1}$;

q' is independently an integer of 1 to 20 for each (C$_{q'}$H$_{2q'}$—O); q is an integer of 1 to 20; w is an integer of 0 to 10; v is an integer of 0 to 6; each v' is independently an integer of 0 to 6; g is an integer of 1 to 3; each D is independently and non-directionally selected from the group set forth for D above, with the proviso that the ring containing D has from 3 to 10 ring atoms; each W is independently selected from the group consisting of N, CR', and SIR';

R$_h$ is an alkylene group having at least two carbon atoms and containing at least one catenary ether oxygen atom; and R$_f$ is fluoroalkyl or fluoroether.

7. The process of claim 6 wherein said R$_f$ is perfluoroalkyl or perfluoroether and contains from 1 to 20 carbon atoms; said R$_h$ contains from 2 to 12 carbon atoms; and said D is selected from the group consisting of —O—, —C(=O)—, a covalent bond, and combinations thereof.

8. The process of claim 7 wherein said R$_h$ contains from 2 to 8 carbon atoms and said D is —O—.

9. The process of claim 6 wherein said R$_h$ is represented by the general formula (C$_s$H$_{2s}$O)$_t$C$_r$H$_{2r}$—, wherein s is independently an integer of 1 to 10 for each (C$_s$H$_{2s}$O), t is an integer of 1 to 6, and r' is an integer of 1 to 10.

10. The process of claim 9 wherein said s is an integer of 2 to 7, said t is an integer of 1 to 3, and said r' is an integer of 1.

11. The process of claim 6 wherein said R$_f$ is represented by the formula —C$_q$F$_{2q}$X', where q is as defined in claim 6 and X' is hydrogen or fluorine.

12. The process of claim 6 wherein said R$_f$ is represented by the formula —R$_{f'}$—R$_{h'}$, where R$_{f'}$ is a linear or branched, perfluorinated or partially-fluorinated alkylene group having from 1 to 10 carbon atoms and optionally containing one or more catenary ether oxygen atoms, and R$_{h'}$ is a linear or branched alkyl group having from 1 to 14 carbon atoms and optionally containing one or more catenary ether oxygen atoms.

13. The process of claim 6 wherein said R$_f$ is represented by the formula —(C$_x$F$_{2x}$O)$_z$C$_y$F$_{2y+1}$, where x is independently an integer of 1 to 10 for each (C$_x$F$_{2x}$O), y is an integer of 1 to 10, and z is an integer of 1 to 10.

14. The process of claim 1 wherein said smectic or latent smectic liquid crystal compound of said composition (b) has at least one fluorinated terminal portion.

15. The process of claim 14 wherein said fluorinated terminal portion comprises at least one perfluoroether group.

16. Fluorine-containing liquid crystal compounds represented by the general formula I:

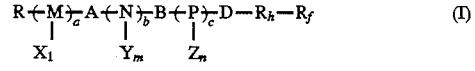

where M, N, P, A, B, X, Y, Z, a, b, c, l, m, n, D, and R are as defined in claim 6; R$_h$ is represented by the directional general formula —(C$_3$H$_{2s}$O)$_t$C$_r$H$_{2r}$—, wherein s is independently an integer of 3 to 10 for each (C$_s$H$_{2s}$O), t is an integer of 1 to 6, and r' is an integer of 1 to 10; and R$_f$ is fluoroether;

with the proviso that the compounds do not exhibit at least one tilted smectic mesophase.

17. The compounds of claim 16 wherein said s is an integer of 3 to 7, said t is an integer of 1 to 3, and said r' is an integer of 1 to 5.

18. The compounds of claim 17 wherein said t is an integer of 1 to 2 and said r' is an integer of 1.

19. The compounds of claim 16 wherein said R$_h$ has from 4 to 12 carbon atoms.

20. The compounds of claim 16 wherein said R$_f$ is perfluoroether.

21. The compounds of claim 20 wherein said $R_f$ is represented by the formula $-(C_xF_{2x}O)_zC_yF_{2y+1}$, where x is independently an integer of 1 to 10 for each $(C_xF_{2x}O)$, y is an integer of 1 to 10, and z is an integer of 1 to 10.

22. A mixture of liquid crystal compounds prepared by the process of claim 1, wherein said alkylene group has at least 4 carbon atoms.

23. A mixture of liquid crystal compounds prepared by the process of claim 21 and having a cone tilt angle between about 10 and about 35 degrees.

24. A mixture of liquid crystal compounds comprising at least one compound of claim 16.

25. A liquid crystal display device containing the mixture of claim 22.

26. A liquid crystal display device containing the mixture of claim 23.

27. A liquid crystal display device containing the mixture of claim 24.

28. A process for controlling the cone tilt angle of a tilted smectic liquid crystal composition comprising the step of combining (a) at least one liquid crystal composition comprising at least one smectic or latent smectic liquid crystal compound comprising (i) an aliphatic fluorocarbon terminal portion represented by the formula $-D-R_h-R_f$, where $R_h$ contains from 2 to 12 carbon atoms and is represented by the general formula $(C_sH_{2s}O)_tC_rH_{2r'}-$, wherein s is independently an integer of 1 to 10 for each $(C_sH_{2s}O)$, t is an integer of 1 to 6, and r' is an integer of 1 to 10; $R_f$ is perfluoroalkyl or perfluoroether and contains from 1 to 20 carbon atoms; and D is selected from the group consisting of $-O-$, $-C(=O)-$, a covalent bond, and combinations thereof; (ii) an aliphatic hydrocarbon terminal portion; and (iii) a central core connecting said terminal portions; and (b) at least one liquid crystal composition comprising at least one fluorine-containing, smectic or latent smectic liquid crystal compound; with the provisos that at least one of said compositions (a) and (b) comprises at least one chiral liquid crystal compound and that said combining of compositions (a) and (b) provides an optically active, tilted chiral smectic liquid crystal composition.

29. Fluorine-containing liquid crystal compounds represented by the general formula I:

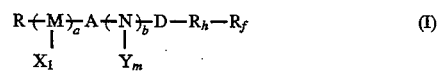

where M is pyrimidine; N is phenyl; A is a covalent bond; X and Y hydrogen; a and b are integers of 1; l is an integer of 2; m is an integer of 4; D is $-O-$; R is an alkyl, fluoroalkyl, alkoxy, or fluoroalkoxy group having from 4 to 8 carbon atoms and optionally containing one or more catenary ether oxygen atoms; $R_h$ has from about 4 to about 8 carbon atoms and is represented by the directional general formula $-(C_sH_{2s}O)_tC_{r'}H_{2r'}-$, wherein s is independently an integer of 3 to 7 for each $(C_sH_{2s}O)$, t is an integer of 1 to 2, and r' is an integer of 1; and $R_f$ is a perfluoroether group represented by the formula $-(C_xF_{2x}O)_zC_yF_{2y+1}$, where x is independently an integer of 1 to 10 for each $(C_xF_{2x}O)$, y is an integer of 1 to 10, and z is an integer of 1 to 10; with the proviso that the compounds do not exhibit at least one tilted smectic mesophase.

* * * * *

UNITED STATES PATENT AND TRADEMARK OFFICE
CERTIFICATE OF CORRECTION

PATENT NO.     : 5,658,491 B1
DATED          : August 19, 1997
INVENTOR(S)    : Kistner et al.

It is certified that error appears in the above-identified patent and that said Letters Patent is hereby corrected as shown below:

Title page,
Item [21], in the Application No. delete "542,179" and insert therefore --08/542,179 --.
Item [56], for the reference "Molecular Crystals Liquid Crystals 67, 235" delete "(9181)"and insert therefor --1981 --.

Column 1,
Line 31, delete "Compound" and insert therefore -- compound --.

Column 2,
Line 65, delete "janulis" and insert therefore -- Janulis --.

Column 4,
Line 17, delete "allcyclic" and insert therefor -- alicyclic --.
Line 18, delete "allcyclic" and insert therefor -- alicyclic --.

Column 6,
Line 23, delete "SIR'" and insert therefor -- SiR' --.
Line 32, delete "Can" and insert therefore -- can --.
Line 39, delete "Which" and insert therefor -- which --.

Column 7,
Line 4, delete "janulis" and insert therefore -- Janulis --.
Line 53, delete "Cone" and insert therefore -- cone --.

Column 13,
Line 62, delete "I" and insert therefore -- 1 --.

UNITED STATES PATENT AND TRADEMARK OFFICE
CERTIFICATE OF CORRECTION

PATENT NO. : 5,658,491 B1
DATED : August 19, 1997
INVENTOR(S) : Kistner et al.

It is certified that error appears in the above-identified patent and that said Letters Patent is hereby corrected as shown below:

Column 16,
Line 52, delete "10" after "mol),".

Column 17,
Line 33, delete "I" and insert therefore --1 --.

Column 20,
Line 11, delete "mmoI" and insert therefore -- mmol --.

Column 21 and 22,
Example 17, delete "$OC_4F_9$" and insert therefor -- $OCF_3$ --.

Column 38,
Line 53, delete "$C_3$" and insert therefore -- $C_s$ --.

Column 39,
Line 9, delete "21" and insert therefore -- 22 --.

Signed and Sealed this

Thirtieth Day of July, 2002

Attest:

JAMES E. ROGAN
Attesting Officer *Director of the United States Patent and Trademark Office*

UNITED STATES PATENT AND TRADEMARK OFFICE
CERTIFICATE OF CORRECTION

PATENT NO.    : 5,658,491
DATED         : August 19, 1997
INVENTOR(S)   : Kistner, John F.

It is certified that error appears in the above-identified patent and that said Letters Patent is hereby corrected as shown below:

Column 27,
Lines 27 and 66, delete "(nonfluorobutoxy)" and insert therefore -- (nonafluorobutoxy) --.

Column 28,
Lines 17, 28, 40, 52, 64, delete "(nonfluorobutoxy)" and insert therefore
-- (nonafluorobutoxy) --.

Column 29,
Lines 9, 20, 31, 44 and 57, delete "(nonfluorobutoxy)" and insert therefore
-- (nonafluorobutoxy) --.

Column 30,
Lines 6, 20, 35, 47 and 60, delete "(nonfluorobutoxy)" and insert therefore
-- (nonafluorobutoxy) --.

Column 31,
Lines 4, 16, 29, 42 and 56, delete "(nonfluorobutoxy)" and insert therefore
-- (nonafluorobutoxy) --.

Column 32,
Lines 1, 16, 31, 45 and 57, delete "(nonfluorobutoxy)" and insert therefore
-- (nonafluorobutoxy) --.

Column 33,
Lines 6, 24, 37, 51 and 64, delete "(nonfluorobutoxy)" and insert therefore
-- (nonafluorobutoxy) --.

Signed and Sealed this

Eleventh Day of March, 2003

JAMES E. ROGAN
*Director of the United States Patent and Trademark Office*